US011827620B2

(12) United States Patent
Rando et al.

(10) Patent No.: US 11,827,620 B2
(45) Date of Patent: Nov. 28, 2023

(54) COMPOUNDS AND USES THEREOF FOR DETECTION OF TARGET MOLECULES IN A SAMPLE

(71) Applicant: UNIVERSITE DE GENEVE, Geneva (CH)

(72) Inventors: Gianpaolo Rando, Crissier (CH); Nicolas Winssinger, Nyon (CH); Eric Lindberg, McLean, VA (US); Marcello Anzola, Geneva (CH)

(73) Assignee: UNIVERSITE DE GENEVE, Geneva (CH)

( * ) Notice: Subject to any disclaimer, the term of this patent is extended or adjusted under 35 U.S.C. 154(b) by 1262 days.

(21) Appl. No.: 16/340,711

(22) PCT Filed: Oct. 12, 2017

(86) PCT No.: PCT/EP2017/076121
§ 371 (c)(1),
(2) Date: Apr. 10, 2019

(87) PCT Pub. No.: WO2018/069470
PCT Pub. Date: Apr. 19, 2018

(65) Prior Publication Data
US 2019/0315713 A1    Oct. 17, 2019

(30) Foreign Application Priority Data

Oct. 13, 2016 (EP) .................................. 16193785

(51) Int. Cl.
| | |
|---|---|
| *C07D 401/12* | (2006.01) |
| *C07C 205/56* | (2006.01) |
| *C12Q 1/6816* | (2018.01) |
| *C07C 205/57* | (2006.01) |
| *C08L 71/02* | (2006.01) |
| *C08L 77/00* | (2006.01) |
| *C07F 9/655* | (2006.01) |
| *C09B 29/08* | (2006.01) |
| *G01N 21/00* | (2006.01) |
| *G01N 21/62* | (2006.01) |
| *G01N 21/63* | (2006.01) |
| *G01N 21/64* | (2006.01) |

(52) U.S. Cl.
CPC .......... *C07D 401/12* (2013.01); *C07C 205/56* (2013.01); *C07C 205/57* (2013.01); *C12Q 1/6816* (2013.01); *C07F 9/65522* (2013.01); *C08L 71/02* (2013.01); *C08L 77/00* (2013.01); *C09B 29/0813* (2013.01); *G01N 21/00* (2013.01); *G01N 21/62* (2013.01); *G01N 21/63* (2013.01); *G01N 21/64* (2013.01); *G01N 21/6428* (2013.01)

(58) Field of Classification Search
CPC .................................................... C07D 401/12

USPC .......................................................... 546/10
See application file for complete search history.

(56) References Cited

U.S. PATENT DOCUMENTS

| | | | |
|---|---|---|---|
| 4,431,440 A | * | 2/1984 | Bhalla ..................... A01N 43/54 |
| | | | 504/240 |
| 5,443,986 A | | 8/1995 | Haughland et al. |
| 5,798,273 A | | 8/1998 | Shuler et al. |

OTHER PUBLICATIONS

Anzola, M. et al. "Turn On of a Ruthenium(II) Photocatalyst by DNA-Templated Ligation" *Chem. Eur. J.*, 2019, pp. 334-342, vol. 25.
Briones, C. et al. "Applications of peptide nucleic acids (PNAs) and locked nucleic acids (LNAs) in biosensor development" *Anal. Bioanal. Chem.*, 2012, pp. 3071-3089, vol. 402, No. 10.
Cai, Y. et al. "Detection and quantification of beef and pork materials in meat products by duplex droplet digital PCR" *PLoS One*, Aug. 3, 2017, pp. 1-12, vol. 12, No. 8.
Diwu, Z. et al. "Spectral Properties and Biological Applications of ELF® Enzyme Substrates That Yield Fluorescent Precipitates at the Enzymatic Activity Sites" *Conference on Advances in Fluorescence Sensing Technology IV*, Jan. 1999, SPIE, pp. 265-274, vol. 3602.
Doessing, H. et al. "Locked and Unlocked Nucleosides in Functional Nucleic Acids" *Molecules*, 2011, pp. 4511-4526, vol. 16.
Holtzer, L. et al. "Nucleic Acid Templated Chemical Reaction in a Live Vertebrate" *ACS Central Science*, 2016, pp. 1-7.
Manicardi, A. et al. "Effect of chirality in gamma-PNA: PNA interaction, another piece in the picture" *Artificial DNA: PNA & XNA*, 2014, pp. e1131801-1-e1131801-4, vol. 5, No. 3.
Moccia, M. et al. "Insights on chiral, backbone modified peptide nucleic acids: Properties and biological activity" *Artificial DNA: PNA & XNA*, 2014, pp. e1107176-1-e1107176-15, vol. 5, No. 3.
Naleway, J.J. et al. "Synthesis and Use of New Fluorogenic Precipitating Substrates" *Tetrahedron Letters*, 1994, pp. 8569-8672, vol. 35, No. 46.
Pianowski, Z. L. et al. "Fluorescence-based detection of single nucleotide permutation in DNA via catalytically templated reaction" *Chem. Commun.*, 2007, pp. 3820-3822, vol. 37.
Prier, C. K. et al. "Visible Light Photoredox Catalysis with Transition Metal Complexes: Applications in Organic Synthesis" *Chem. Rev.*, 2013, pp. 5322-5363, vol. 113.
Sadhu, K. K. et al. "In cellulo protein labelling with Ru-conjugate for luminescence imaging and bioorthogonal photocatalysis" *Chem. Commun.*, 2015, pp. 16664-16666, vol. 51.
Sadhu, K. K. et al. "Detection of miRNA in Live Cells by Using Templated $Ru^{II}$—Catalyzed Unmasking of a Fluorophore" *Chem. Eur. J.*, 2013, pp. 8182-8189, vol. 19.

(Continued)

*Primary Examiner* — Niloofar Rahmani
(74) *Attorney, Agent, or Firm* — SALIWANCHIK, LLOYD & EISENSCHENK

(57) ABSTRACT

The present invention relates to new profluorophores and conjugates thereof and their use for the detection of target molecule in a sample, in particular nucleic acid target molecules. The invention relates to new profluorophores and new fluorophores and methods of use thereof particularly useful in the fields of diagnostics and quality control.

19 Claims, 7 Drawing Sheets

Specification includes a Sequence Listing.

(56) References Cited

OTHER PUBLICATIONS

Spaniolas, S. et al. "Authentication of Coffee by means of PCR-RFLP Analysis and Lab-on a-Chip Capillary Electrophoresis" *J. Agric. Food Chem.*, 2006, pp. 7466-7470, vol. 54, No. 20.

Strommenger, B. et al. "Multiplex PCR Assay for Simultaneous Detected of Nine Clinically Relevant Antibiotic Resistance Genes in *Staphylococcus aureus*" *Journal of Clinical Microbiology*, Sep. 2003, pp. 4089-4094, vol. 41, No. 9.

Zhou, L. et al. "Localizable and Photoactivatable Fluorophore for Spatiotemporal Two-Photon Bioimaging" *Analytical Chemistry*, 2015, pp. 5626-5631, vol. 87.

Written Opinion in International Application No. PCT/EP2017/076121, dated Jan. 19, 2018, pp. 1-10.

\* cited by examiner

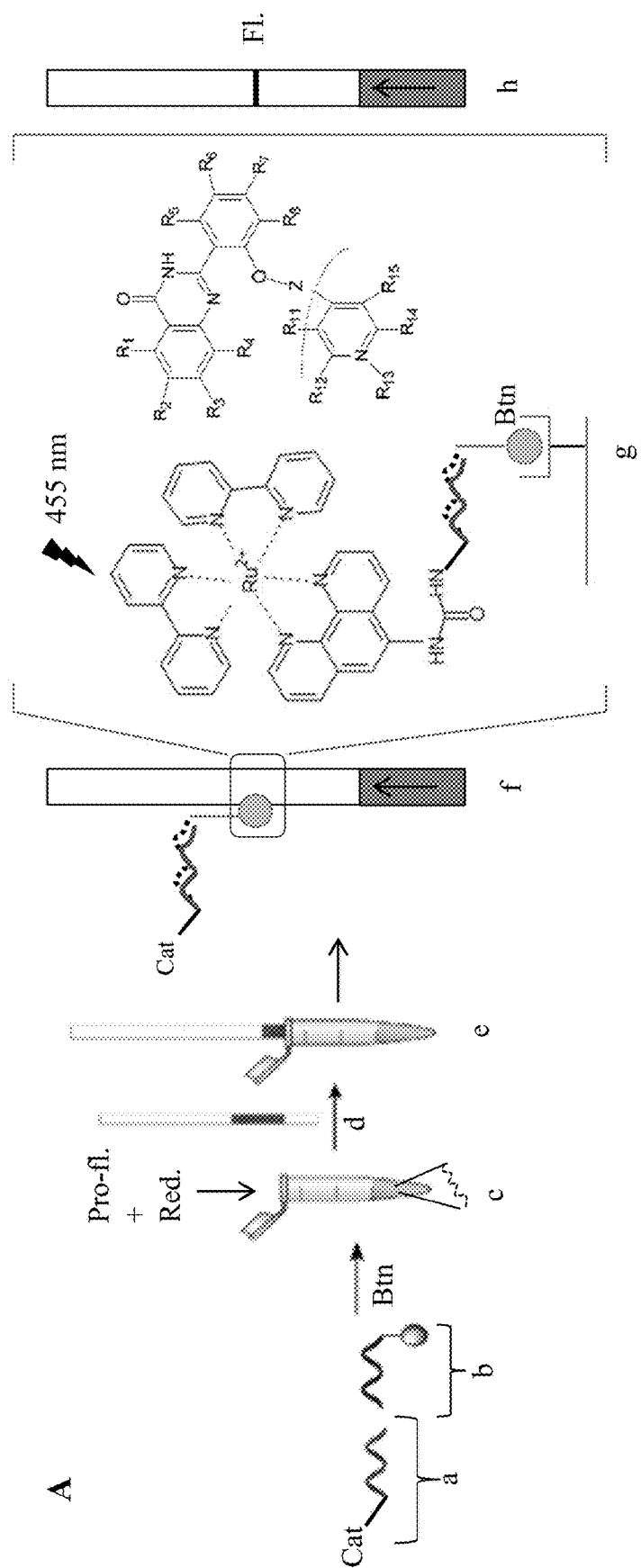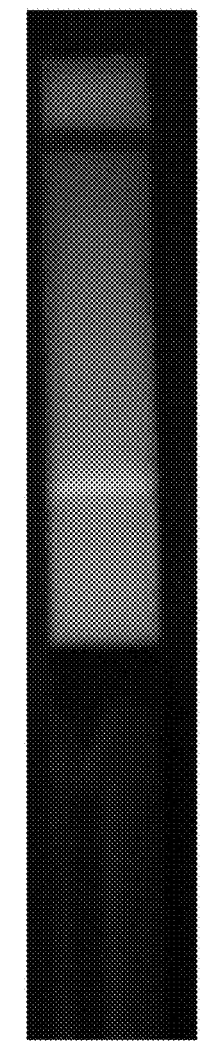
Figure 1

```
Pork Vs. Beef
Conserved         *      **    *     *    *     *    *   *    *    *     *        *  *        *   *        *    *     * *   * *     *    *    *   *    *
Pork-----------   GCGCTGAACTAGGTCAGCCCGAACCCTACTTGGCGATGATCAAATCTATAAATGTAATTGTTACAGCTCATGCC
Beef-----------   GCC-TGAATTAGGCCAACCCGAACTCTGCTCGGAGACGACCAAATCTACAACGCAGTTGTAACCGCACACGCA
Horse----------   GTGCTGAATTAGGCCAACCTGGGACCCTACTAGGAGATGATCAGATCTACAATGTCATTGTAACCGCCCATGCA
Guinea fowl----   GCGCAGAACTAGGACAACCAGGAGACCCTTTTAGGGACGACCAAATTTATAATGTAATCGTCACAGCCCATGCC
Turkey---------   GGTGCAGAACTGGGACAACCTGGGACACTCCTAGGAGACGACCAAATCTATAACGTAATCGTCACAGCCCATGC
Chicken--------   GCGCAGAACTAGGACAGCCCGGAACTCTCTTAGGAGACGATCAAATTTACAATGTAATCGTCACAGCCCATGCT
Donkey---------   GTGCTGAATTAGGTCAACCTGGGACCCCTGCTGGGAGATGATCAGATCTACAATGTTATTGTAACTGCCCATGCA
Monkey---------   GAGCTGAACTAGGCCAACCCGGTAGTTTACTAGGTAACGACCATATCTATAATGTCATTGTGACAGCCCATGCA
Human----------   GAGCCGAGCTGGGCCAGCCAGGCAAGCTCCTAGGAGATGATAACCACAATCTATAATGTCTACAACGTTATCGTCATCGTTACAGCCCATGCA
Rat------------   GAGCTGAACTAGGACAGCCAGCCAGGTGCACTCCTAGGAGATGACCAAATTTACAATGTCTATAATGTTACAATGTTATCGTAACTGCCCATGCT
Mouse----------   GAGCAGAATTAGGTCAACCAGCCTGGGCAGTTGCTTGGACATTGCTTGGAGATGACCAAATCTATAATGTAGTTGTAACGGCTCATGCT
Dromedarius----   GTGCTGAATTGGGGCAGCCCAGCAGCCCGGGACAGCCCGGAGCGTTGCTTGGAGACGACCAAATCTATAACGTAGTTGTAACAGCTCATGCT
Camel----------   GCGCTGAATTGGGACAGCCCAACGCCCGGACGTTGCTTGGAGACGACCAAATCTATAACGTATAACGTATAAACGTAGTTGTAACAGTCATGCT
Lamb-----------   GCGCCGAACTAGGCCAACCCGAACCCGAACTCTACTCGGAGATGACCAAATCTACAACGTAATTGTAACCGCACATGCA
Goat-----------   GCGCCGAACTAGGTCAACCCGAACCCGAACCCTACTTGGAGATGACCAGATCTACAATGTAATTGTAACTGCACACGCA
```

Figure 3

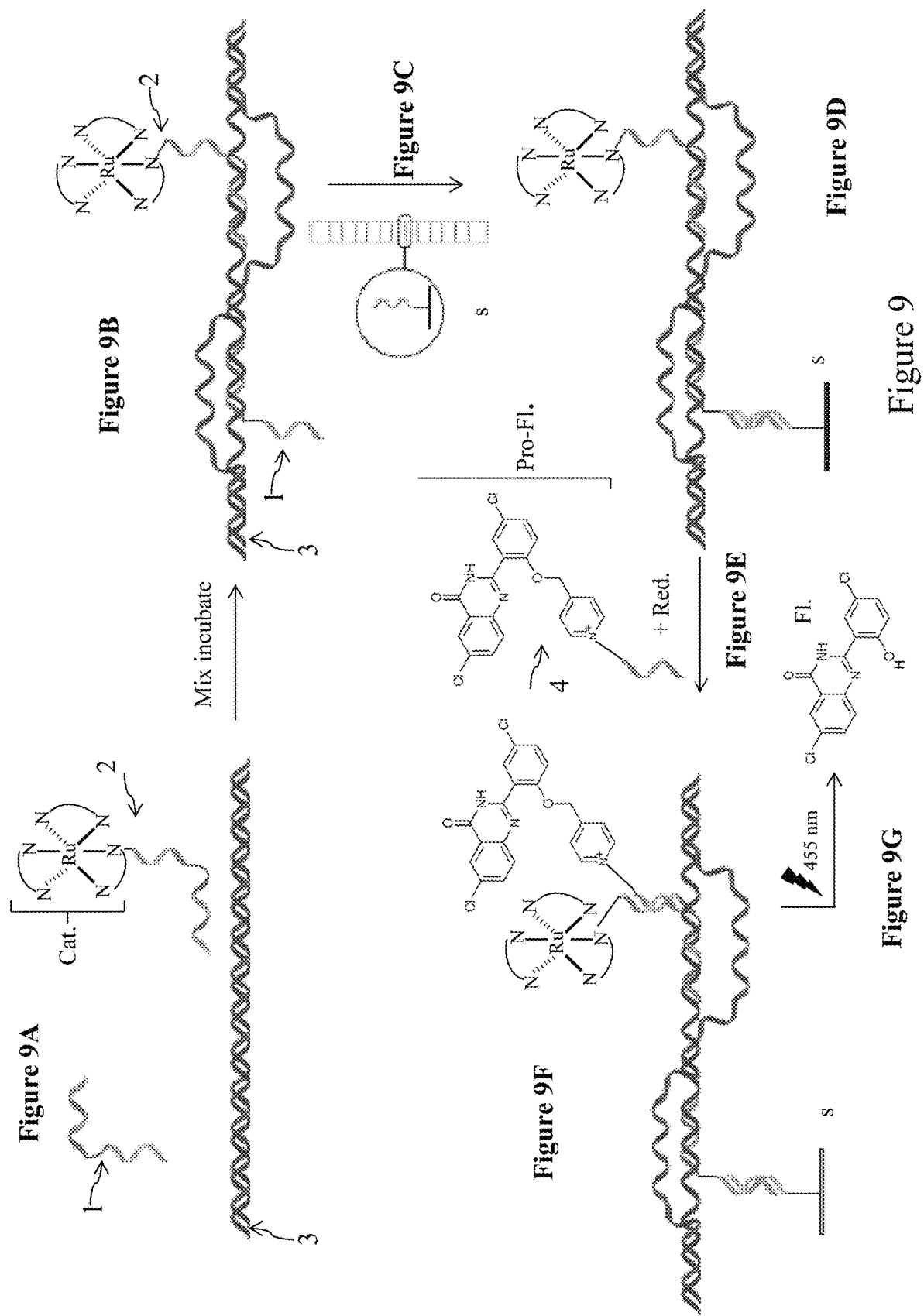

SEQUENCE LISTING

<160> NUMBER OF SEQ ID NOS: 19

<210> SEQ ID NO 1
<211> LENGTH: 12
<212> TYPE: DNA
<213> ORGANISM: Artificial Sequence
<220> FEATURE:
<223> OTHER INFORMATION: Nucleic acid sequence 1 of probe specific for
      porcine DNA

<400> SEQUENCE: 1
cttgggatga ac                                                          12

<210> SEQ ID NO 2
<211> LENGTH: 14
<212> TYPE: DNA
<213> ORGANISM: Artificial Sequence
<220> FEATURE:
<223> OTHER INFORMATION: Nucleic acid sequence 2 of probe specific for
      porcine DNA

<400> SEQUENCE: 2
ctactagttt agat                                                        14

<210> SEQ ID NO 3
<211> LENGTH: 40
<212> TYPE: DNA
<213> ORGANISM: Artificial Sequence
<220> FEATURE:
<223> OTHER INFORMATION: Nucleic acid sequence of porcine DNA fragment

<400> SEQUENCE: 3
cagcccggaa ccctacttgg cgatgatcaa atctataatg                            40

<210> SEQ ID NO 4
<211> LENGTH: 15
<212> TYPE: DNA
<213> ORGANISM: Artificial Sequence
<220> FEATURE:
<223> OTHER INFORMATION: Nucleic acid sequence 4 of probe specific for
      porcine DNA

<400> SEQUENCE: 4
cgcgacttga tccag                                                       15

<210> SEQ ID NO 5
<211> LENGTH: 74
<212> TYPE: DNA
<213> ORGANISM: Artificial Sequence
<220> FEATURE:
<223> OTHER INFORMATION: Pork DNA region

<400> SEQUENCE: 5
gcgctgaact aggtcagccc ggaaccctac ttggcgatga tcaaatctat aatgtaattg      60
ttacagctca tgcc                                                        74

<210> SEQ ID NO 6
<211> LENGTH: 73
<212> TYPE: DNA
<213> ORGANISM: Artificial Sequence
<220> FEATURE:
<223> OTHER INFORMATION: Beef DNA region

<400> SEQUENCE: 6
gcctgaatta ggccaacccg gaactctgct cggagacgac caaatctaca acgcagttgt      60
aaccgcacac gca 73

<210> SEQ ID NO 7
<211> LENGTH: 74
<212> TYPE: DNA
<213> ORGANISM: Artificial Sequence
<220> FEATURE:
<223> OTHER INFORMATION: Horse DNA region

<400> SEQUENCE: 7
gtgctgaatt aggccaacct gggaccctac taggagatga tcagatctac aatgtcattg   60
taaccgccca tgca   74

<210> SEQ ID NO 8
<211> LENGTH: 74
<212> TYPE: DNA
<213> ORGANISM: Artificial Sequence
<220> FEATURE:
<223> OTHER INFORMATION: Guinea fowl DNA region

<400> SEQUENCE: 8
gcgcagaact aggacaacca gggacccttt taggggacga ccaaatttat aatgtaatcg   60
tcacagccca tgcc   74

<210> SEQ ID NO 9
<211> LENGTH: 74
<212> TYPE: DNA
<213> ORGANISM: Artificial Sequence
<220> FEATURE:
<223> OTHER INFORMATION: Turkey DNA region

<400> SEQUENCE: 9
ggtgcagaac tgggacaacc tgggacactc ctaggagacg accaaatcta taacgtaatc   60
gtcacagccc atgc   74

<210> SEQ ID NO 10
<211> LENGTH: 74
<212> TYPE: DNA
<213> ORGANISM: Artificial Sequence
<220> FEATURE:
<223> OTHER INFORMATION: Chicken DNA region

<400> SEQUENCE: 10
gcgcagaact aggacagccc ggaactctct taggagacga tcaaatttac aatgtaatcg   60
tcacagccca tgct   74

<210> SEQ ID NO 11
<211> LENGTH: 74
<212> TYPE: DNA
<213> ORGANISM: Artificial Sequence
<220> FEATURE:
<223> OTHER INFORMATION: Donkey DNA region

<400> SEQUENCE: 11
gtgctgaatt aggtcaacct gggaccctgc tgggagatga tcagatctac aatgttattg   60
taactgccca tgca   74

<210> SEQ ID NO 12
<211> LENGTH: 74
<212> TYPE: DNA
<213> ORGANISM: Artificial Sequence
<220> FEATURE:
<223> OTHER INFORMATION: Monkey DNA region

```
<400> SEQUENCE: 12
gagctgaact aggccaaccc ggtagtttac taggtagtga ccatatctat aatgtcattg      60
tgacagccca tgca                                                       74

<210> SEQ ID NO 13
<211> LENGTH: 74
<212> TYPE: DNA
<213> ORGANISM: Artificial Sequence
<220> FEATURE:
<223> OTHER INFORMATION: Human DNA region

<400> SEQUENCE: 13
gagccgagct gggccagcca ggcaaccttc taggtaacga ccacatctac aacgttatcg      60
tcacagccca tgca                                                       74

<210> SEQ ID NO 14
<211> LENGTH: 74
<212> TYPE: DNA
<213> ORGANISM: Artificial Sequence
<220> FEATURE:
<223> OTHER INFORMATION: Rat DNA region

<400> SEQUENCE: 14
gagctgaact aggacagcca ggcgcactcc taggagatga ccaaatctat aatgtcatcg      60
tcacagccca tgca                                                       74

<210> SEQ ID NO 15
<211> LENGTH: 74
<212> TYPE: DNA
<213> ORGANISM: Artificial Sequence
<220> FEATURE:
<223> OTHER INFORMATION: Mouse DNA region

<400> SEQUENCE: 15
gagcagaatt aggtcaacca ggtgcacttt taggagatga ccaaatttac aatgttatcg      60
taactgccca tgct                                                       74

<210> SEQ ID NO 16
<211> LENGTH: 74
<212> TYPE: DNA
<213> ORGANISM: Artificial Sequence
<220> FEATURE:
<223> OTHER INFORMATION: Dromedarius DNA region

<400> SEQUENCE: 16
gtgctgaatt ggggcagcct gggacattgc ttggagatga ccaaatctat aatgtagttg      60
taacggctca tgct                                                       74

<210> SEQ ID NO 17
<211> LENGTH: 74
<212> TYPE: DNA
<213> ORGANISM: Artificial Sequence
<220> FEATURE:
<223> OTHER INFORMATION: Camel DNA region

<400> SEQUENCE: 17
gcgctgaatt gggacagccc gggacgttgc ttggagacga ccaaatctat aacgtagttg      60
taacagctca tgct                                                       74

<210> SEQ ID NO 18
```

```
<211> LENGTH: 74
<212> TYPE: DNA
<213> ORGANISM: Artificial Sequence
<220> FEATURE:
<223> OTHER INFORMATION: Lamb DNA region

<400> SEQUENCE: 18
gcgccgaact aggccaaccc ggaactctac tcggagatga ccaaatctac aacgtaattg    60
taaccgcaca tgca                                                     74

<210> SEQ ID NO 19
<211> LENGTH: 74
<212> TYPE: DNA
<213> ORGANISM: Artificial Sequence
<220> FEATURE:
<223> OTHER INFORMATION: Goat DNA region

<400> SEQUENCE: 19
gcgccgaact aggtcaaccc ggaacccta c ttggagatga ccagatctac aatgtaattg    60
taactgcaca cgca                                                     74
```

COMPOUNDS AND USES THEREOF FOR DETECTION OF TARGET MOLECULES IN A SAMPLE

CROSS-REFERENCE TO RELATED APPLICATION

This application is the U.S. national stage application of International Patent Application No. PCT/EP2017/076121, filed Oct. 12, 2017.

The Sequence Listing for this application is labeled "Seq-List.txt" which was created on Mar. 19, 2019 and is 6 KB. The entire content of the sequence listing is incorporated herein by reference in its entirety.

FIELD OF THE INVENTION

The present invention relates to profluorophores that precipitate at the site of reaction with a target molecule under photoredox catalysis and their use for detection of said target molecule in a sample.

BACKGROUND OF THE INVENTION

There are increasing needs for signal detection in diagnostics and quality assurance (monitoring traceability, shelf life, sourcing, safety, counterfeit, compliance) applications. In particular, in the field of food industry, there are increasing needs for the detection of the presence of ingredients and bacteria to give immediate verification of the authenticity, compliance and quality of food products. The customer demand comes in particular from food manufacturers, retailers, trade organizations and governmental agencies that control the integrity of the supply chain. This integrity is particularly important for end consumers like people who cannot eat specific foods for medical (e.g. allergies, diet) or personal reasons (e.g. religion). Currently, there is no test that could be easily performed by non-scientist personnel to verify food ingredients at any time and conditions, thus organisations are obliged to entrust information given by a third party provider (i.e. certificate) or send samples to a laboratory service. Since animals, plants and micro-organisms contain specific DNA today more than 300'000 species can be identified through a small region of the genome known as a "DNA barcode" that could be thus used to identify food ingredients. Although DNA sequencing costs are decreasing, the availability of such tests is out of reach for untrained personnel as the standard approach is to isolate and sequence the 650 bp (base pair)-long barcode DNA region and to compare the results with a database of known species (e.g. www.ibol.org). Thus, this method is long, prone to contaminations, requires a laboratory-based sample preparation, a use of specialized equipment and advanced knowledge to interpret results of analysis.

Signal detection in imaging and diagnostic applications is frequently achieved with various dyes, e.g. fluorescence dyes. Fluorophores like rhodamine and azidorhodamines do not provide spatial resolution information since they do not precipitate at the reaction site and other fluorophores just diffuse all around, dispersing the signal and preventing the obtaining of a discrimination of read-out into multiplexed bands/codes. Therefore, those dyes are inadapted to subcellular resolution. The use of another known dye, viologen (e.g. paraquat) often used as a redox indicator, is limited in food applications due to its toxicity and its low sensitivity requires high concentration for achieving naked eyes detection. Quinazoline dyes have been developed to provide signal information with subcellular resolution since they precipitate at the site of reaction. For this purpose, colorless and soluble pro-fluorophores have been designed based on a quinazolinone precipitating dye (QPD) conjugated to an azide trigger group ($N_3$-QPD) that, upon photocatalytic reaction in presence of a catalyst (e.g. ruthenium-based catalyst, e.g. Ru(bpy)$_3$Cl$_2$) and reducing agent (e.g. sodium ascorbate, NaAsc etc.) which is triggered by light (e.g. 455 nm), converts into a fluorescent molecule and precipitates as a Quinazolinone precipitating dye (QPD). In this reaction, photoexcitation of Ru-based catalyst reduces the azide that is in the vicinity of the catalyst, which, in turn, leads to immolation of the linker between the azide and the fluorophore in the pro-fluorophore molecule and thus unmasks a fluorescent dye (so called reductive cleavage or unmasking). Due to the dye precipitation upon unmasking, the fluorescence appears where the reaction takes place and thus a reported signal retains spatial resolution information (Holtzer et al., 2016, *ACS Central Science*, 10.1021/acscentsci.6b00054; Sadhu et al., 2015, *Chem. Commun.*, 51: 16664-6). Based on the fact that the transition metal (e.g. Ru) acts photocatalytically, the reaction is temporally controlled and the reagents can be conveniently handled and mixed without risk of premature reaction. Further, since this reaction does not use enzymatic amplifications, the used reagents are more stable and can be used in various environments. This technique can be used for in cellulo visualizing of proteins tagged with Ru-based catalyst (Sadhu et al., 2015, supra) or in nucleic acid template reactions for in vivo visualizing target microRNAs (Holtzer et al., 2016, supra). However, the limitations of those fluorophores allowing spatial detection still need to be improved to reduce assay time and allow incorporation into disposable detection tests. Therefore, there is a need for the development of new fluorophores allowing high efficient detection and suitable for portable and disposable detection systems.

SUMMARY OF THE INVENTION

The invention is directed to a new pro-fluorophore (e.g. fluorophore precursor or fluorogenic agent) family that converts into a precipitating product (corresponding fluorophore) upon photoredox catalysis thereof. The invention is based on the finding that fluorophores of the following Formula (I') can be formed through the reaction of this new pro-fluorophore family with a transition metal complex photoredox catalyst.

The invention is in particularly directed to the use of the conversion of those colorless pro-fluorophores upon action of a catalyst, in presence of a reducing agent, into a highly fluorescent product that precipitates at the site of reaction of the catalyst, which is in particular in the field of diagnosis or target substance detection. The pro-fluorophores of the invention have the advantage of a higher precipitating yield than known precipitating dyes and to convert into a corresponding fluorophore having a large Stokes shift (difference in absorbed and emitted wavelength) which allows to measure to detect the emitted signal upon precipitation without sophisticated instrumentation since the emitted wavelength (signal) is easily separated from the excitation wavelength and other noise and which is highly photostable which allows a reliable measurement without signal variations and loss of resolution. The invention is in particular directed to methods of use of such pro-fluorophores in the detection of target small molecules, natural and synthetic nucleic acids, proteins and other macro-molecules in a sample and to detection systems and devices comprising those.

According to one aspect, is provided a pro-fluorophore of Formula (I).

According to another aspect, is provided a method of preparation of a fluorophore of Formula (I') comprising a step of reacting a pro-fluorophore of Formula (I) with a transition metal complex photoredox catalyst, in presence of a reducing agent.

According to another aspect, is provided fluorophores of Formula (I').

According to another aspect, is provided a method for the detection of at least one target molecule (e.g. small molecule, natural and synthetic nucleic acid, peptide or protein) in a sample comprising a step of contacting a composition comprising a pro-fluorophore according to the invention or a conjugate thereof (fluorogenic composition) with said sample.

According to another aspect, is provided a conjugate of a pro-fluorophore of Formula (I), wherein said conjugate is of Formula (II).

According to another aspect, is provided a method of preparation of a pro-fluorophore of Formula (I).

Another aspect of the invention provides a kit for the detection of at least one target molecule in a sample comprising a pro-fluorophore of Formula (I) or a conjugate thereof and, optionally, at least one agent selected among a reducing agent and a further probe for the detection of said target molecule.

DESCRIPTION OF THE FIGURES

FIG. 1 is an illustration of a method of detection of a target DNA molecule (at 10 µM) in a sample as further described in Example 3. A: schematic representation of the main steps of the method of detection comprising: contacting (e) a sample containing a target DNA molecule (c) with a mixture of a catalytic probe (a) such as a PNA conjugated to a transition metal complex photoredox catalyst, and an anchoring probe (b) such as Biotinylated (Btn) PNA, where both probes recognize a portion of the target DNA molecule, with an anchoring substrate in the form of a dipstick containing immobilized streptavidin (d), in presence of a reducing agent (red.) and of a pro-fluorophore of the invention (Pro-fl.) under suitable conditions for the probes to bind the target DNA molecule and for the target molecule to be anchored onto the surface of the anchoring substrate (f); triggering a photoredox catalysis of the pro-fluorophore in the vicinity of the photoredox catalyst bound to the dipstick surface by irradiation (g) and visualizing the formed fluorescent (Fl.) band on the anchoring dipstick surface; B: Image of the dipstick surface positive fluorescent (left) and control (right) bands.

FIG. 3 shows a comparison of one DNA region presented as 5'->3' of 73 bp selected from DNA barcode region of COI gene of 15 animals allowing identifying a DNA minibarcode specifically present in pork as described in Example 2. *: sequence conservation. DNA regions from pork (SEQ ID NO: 5), beef (SEQ ID NO: 6), horse (SEQ ID NO: 7), guinea fowl (SEQ ID NO: 8), turkey (SEQ ID NO: 9), chicken (SEQ ID NO: 10), donkey (SEQ ID NO: 11), monkey (SEQ ID NO: 12), human (SEQ ID NO: 13), rat (SEQ ID NO: 14), mouse (SEQ ID NO: 15), dromedarius (SEQ ID NO: 16), camel (SEQ ID NO: 17), lamb (SEQ ID NO: 18), goat (SEQ ID NO: 19).

FIG. 9 shows an example of templated photoreaction in a method according to the invention as described in Example 7. A: a target dsDNA (3) contacted with an anchoring PNA probe (1) and a catalytic PNA probe (2) comprising conjugated a photoredox catalyst (Cat.); B: hybridization between the probes and target dsDNA; C: the hybridized target dsDNA is contacted with a test strip as an anchoring substrate (s) where the anchoring substrate has an moiety having an affinity for the anchoring probe; D: the hybridized target dsDNA is immobilized on a test strip through the anchoring probe; E: A profluorophore (Pro-Fl.) conjugate (4) comprising a profluorophore (compound 1) conjugated to a probe having an affinity for a portion of the catalytic PNA probe is contacted with the test strip in presence of a reducing agent (Red.); F: The profluorophore conjugate is binding on the catalytic PNA probe in the close proximity of the catalytic PNA probe (2); G: the test strip is subjected to illumination (e.g. LED lamp, 455 nm) to promote the photocatalytic reduction of the Pro-Fl. into the fluorophore (Fl.).

DETAILED DESCRIPTION

Figure 2:
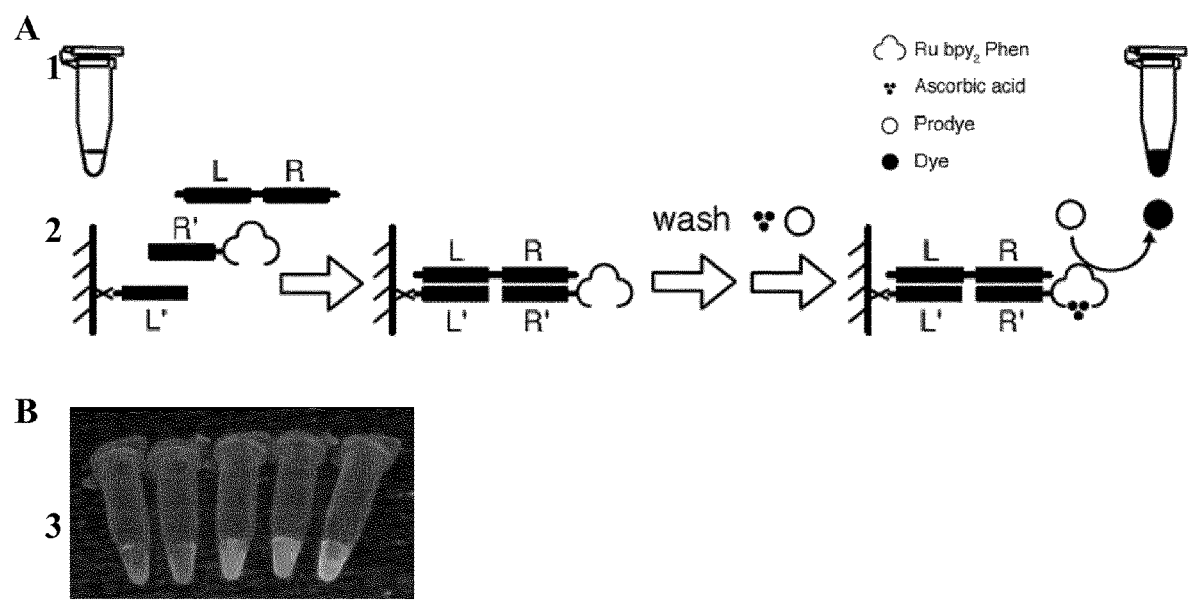
FIG. 2 shows steps (A) and results (B) of a method of the invention for the detection of a target pork DNA fragment in a sample as described in Example 4.

The term "fluorogenic composition" refers to a composition comprising a pro-fluorophore according to the invention either per se or in the form of a conjugate and which is able to undergo a photoredox catalysis when the pro-fluorophore or the conjugate thereof is in the vicinity of a photoredox catalyst and the composition is excited at a wavelength sufficient to excite the photoredox catalyst, thereby generating the corresponding fluorophore.

The term "target molecule" refers to any molecule of interest to be tested for its presence in a sample (e.g. small molecule, natural and synthetic nucleic acid, peptide or protein) such as for example target DNA from a specific origin (such as target mammalian DNA fragment from a specific species (for example from pork, horse, rodent etc.) or a target bacterial DNA fragment (for example DNA from pathogenic bacteria such as *E. Coli, Listeria, Salmonella, Campylobacter, Legionella*) or from toxins of those). According to a particular aspect, target molecules encompass any molecule of interest to be tested for its presence in any material for human or veterinary use such as food (e.g. meat or cheese), feed, pet food, beverages and drinkable preparations. Materials include raw materials, intermediary and finished products, food additives (e.g. enzymes, starter cultures, vitamins) or pharmaceutical or cosmetic preparations. Examples of nucleic acids as target molecules according to the invention encompass DNA and RNA sequences and primers that identify specific species (i.e pork vs beef as in PLoS One., 2017, 12(8):e0181949. doi: 10.1371/journal-.pone.0181949) or specific varieties (i.e Coffee Arabica vs Robusta as in J. *Agric. Food Chem.* 2006 54(20):7466-70) or general families (i.e. microbial antibiotic-resistance genes as in *J. Clin. Microbiol.*, 2003, 41(9). 4089-4094).

The term "probe" refers to a molecule recognizing specifically a target molecule. A nucleic probe acid probe refers to a probe comprising at least one nucleic acid sequence which specifically recognizes at least a region of the target molecule. According to a particular aspect, nucleic probe acid probe comprises nucleic acid of about 1 to about 60 nucleotides, for example from about 4 to about 20 nucleotides, such as from about 4 to about 14 nucleotides, in particular from about 7 to about 14 nucleotides.

According to another particular aspect, nucleic probe acid probes of the invention are PNA or LNA and any mixture of DNA, RNA, PNA or LNA.

The terms "peptide nucleic acid" or "PNA" refers to an artificially synthesized polymer nucleic acid analog similar to DNA or RNA, in which the sugar phosphate backbone of natural nucleic acid has been replaced by a synthetic peptide backbone usually formed from N-(2-amino-ethyl)-glycine units, resulting in an achiral and uncharged mimic. It is chemically stable and resistant to hydrolytic (enzymatic) cleavage. In order to increase binding affinity for some target molecules, probes can be stereochemically modified to render chiral an achiral probe for obtaining binding properties of the so-modified probe which depend on the stereochemistry. For example, modifications of PNA backbones such as gamma-modified PNA have been recently developed for use in diagnostic assays (Manicardi et al., 2014, *Artificial DNA: PNA & XNA*, 5:3, e1131801; Moccia et al., 2014, *Artificial DNA: PNA & XNA*, 5:3, e1107176). According to a particular embodiment, probes according to the invention are PNA probes, in particular gamma PNA probes such as γD-PNA, γL-PNA probes.

The terms "locked nucleic acid" or "LNA" refers to an artificially synthesized modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired and hybridize with DNA or RNA according to Watson-Crick base-pairing rules (Doessing et al., 2011, *Molecules* 2011, 16, 4511-4526).

In a particular embodiment, a probe comprises a PNA probe is selected from a 14-mer, a 7-mer or a 4-mer PNA.

The term "DNA mini-barcode" refers to a DNA sequence that is a fragment of a DNA barcode sequence (typically of about 650 bp). A DNA mini-barcode is usually between 50 to 250 bp, preferentially between 70 and 130 bp, and is specific to one species while being divergent from the same DNA regions of other species to which it was initially compared to during identification process. Because of its shorter length, a DNA mini-barcode can better identify one species in samples in which DNA could be partially degraded (e.g. processed food). One DNA barcode sequence can comprise more than one DNA mini-barcodes.

The term "DNA amplification" refers to a reaction allowing to artificially increasing the number of copies of a particular DNA fragment through iterative replication. The target template can be either DNA or RNA after reverse transcription. Examples of a DNA amplification are an isothermal DNA amplification (LAMP, Loop Mediated isothermal amplification) specific for a pork mitochondrial DNA, nucleic acid sequence based amplification (NASBA), Helicase Dependent Amplification (HDA), recombinase polymerase amplification (RPA), Rolling Circle Amplification (RCA), Single primer isothermal amplification (SPIA), Smart amplification Process Version 2 (SMAP2), Strand Displacement amplification (SDA), Nicking and extension amplification reaction (NEAR), Isothermal and chimeric primer-initiated amplification of nucleic acids (ICAN), Polymerase Spiral Reaction (PSR).

The term "nucleic acid templated reaction" refers to a reaction wherein oligonucleotides that are linked to chemical compounds (e.g. reactants-probe conjugates) recognize specific nucleic acids and hybridize to them thereby bringing the reactants in close proximity to each other (Pianowsky et al., 2007, *Chem. Commun.*, 37: 3820-3822). Compared to random intermolecular reactions, nucleic acid templated reactions occur at a faster rate, which can be a competitive advantage for point-of-need tests based on this chemistry.

The term "alkoxycarbonyl" refers to the group —C(O)OR where R includes "C1-C6 alkyl", "aryl", "heteroaryl", "aryl C1-C6 alkyl", "heteroaryl C1-C6 alkyl" or "heteroalkyl".

The term "alkoxycarbonyl C1-C6 alkyl" refers to C1-C6 alkyl groups having an alkoxycarbonyl substituent, including 2-(benzyloxycarbonyl)ethyl and the like.

Unless otherwise constrained by the definition of the individual substituent, the term "substituted" refers to groups substituted with from 1 to 5 substituents selected from the group consisting of "$C_1$-$C_6$ alkyl," "amino," "aminosulfonyl," "amino carbonyl," "sulfonyl," "alkoxy," "alkoxy carbonyl," "halogen," trihalomethyl, cyano, hydroxy, mercapto, nitro, and the like.

Compounds according to the present invention comprise a compound according to Formula (I) and its geometrical isomers, in particular well known isomers of the quinazoline moiety.

As used herein a kit can contain a "test device" in the form of a "test strip" that allows performing a method of the invention, in particular the detection of DNA/RNA target molecules according to the invention. According to a particular aspect, a test device is made of a material that allows the flow of a solution and molecules contained therein to move by capillarity. Examples of such materials are cellulose esters (including nitrocellulose acetate and cellulose acetate), cellulosic paper, filter paper, tissue paper or porous polymer film. An example of a test device is a "lateral flow strip" device comprising a detection line made of immobilized streptavidin or capture probes and a bottom pouch comprising a pro-fluorophore according to the invention and a reducing agent. A kit according to the invention may further comprise a sampling device.

The term "a sampling device" refers to a device that allows obtaining a sample for use in an assay. Examples of a sampling device comprise a biopsy punch for meat and leaves or a cotton swab for microbes.

The term "a sample crusher" refers to a device that allows disgregating sample material inside a compatible buffer (i.e. Tris 10 mM, EDTA 1 mM, pH 8.0). By breaking the cellular structure of various samples, a sample crusher let target analytes (i.e. DNA) to pass into solution. Sample crushers can be commercially acquired, for example as disposable pestles (Eppendorf) or portable cell disruptors (Xpedition, Zymo Research).

Pro-Fluorophores According to the Invention

According to one aspect, is provided a compound of Formula (I):

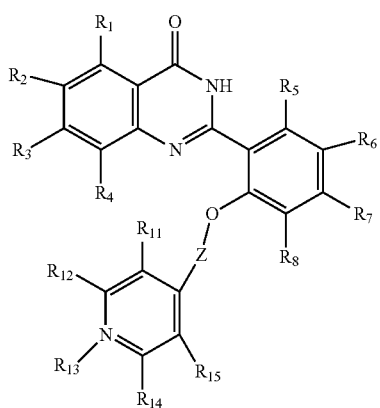

(I)

wherein $R_1$ to $R_8$, $R_{11}$-$R_{12}$ and $R_{14}$-$R_{15}$ are independently selected from hydrogen, hydroxyl, halogen such as chloro, cyano, nitro, optionally substituted $C_1$-$C_{10}$ alkyl, optionally substituted amino $C_1$-$C_{10}$ alkyl, optionally substituted $C_1$-$C_{10}$ alkoxy, $R_{13}$ is selected from optionally substituted $C_1$-$C_{10}$ alkyl such as optionally substituted ethyl (e.g. ethyl), optionally substituted propyl (propyl or N-propyl nitrile) or optionally substituted butyl (e.g. butyl), Z is —$CR_{16}R_{17}$ wherein $R_{16}$ and $R_{17}$ are independently selected from hydrogen and optionally substituted $C_1$-$C_6$ alkyl or any tautomer, isomer, conjugate or salts thereof.

According to another aspect, a counter salt of a pro-fluorophore of the invention is trifluoromethanesulfonate (OTf).

According to another aspect, is provided a pro-fluorophore of Formula (I), wherein $R_1$, $R_3$ to $R_5$ and $R_7$ to $R_8$ are H.

According to another aspect, is provided a pro-fluorophore of Formula (I), wherein $R_{11}$ and $R_{15}$ are H.

According to another aspect, is provided a pro-fluorophore of Formula (I), wherein $R_{11}$-$R_{12}$ and $R_{14}$-$R_{15}$ are H.

According to another aspect, is provided a pro-fluorophore of Formula (I), wherein $R_{12}$ is optionally substituted $C_1$-$C_{10}$ alkyl such as methyl. According to another aspect, is provided a pro-fluorophore of Formula (I), wherein $R_{14}$ is optionally substituted $C_1$-$C_{10}$ alkyl such as methyl.

According to another aspect, is provided a pro-fluorophore of Formula (I) wherein $R_2$ is Cl.

According to another aspect, is provided a pro-fluorophore of Formula (I) wherein $R_2$ is H.

According to another aspect, is provided a pro-fluorophore of Formula (I) wherein $R_6$ is Cl.

According to another aspect, is provided a pro-fluorophore of Formula (I) wherein $R_6$ is H.

According to another aspect, is provided a pro-fluorophore of Formula (I), wherein $R_6$ is optionally substituted $C_1$-$C_{10}$ alkyl.

According to a further embodiment aspect, is provided a provided a pro-fluorophore of Formula (I), wherein $R_6$ is alkoxycarbonyl $C_1$-$C_{10}$ alkyl such as —$CH_2C(O)OMe$.

According to another aspect, is provided a provided a pro-fluorophore of Formula (I), wherein $R_1$-$R_8$ are H.

According to another aspect, is provided a pro-fluorophore of Formula (I) wherein $R_{13}$ is optionally substituted butyl.

According to a further aspect, is provided a pro-fluorophore of Formula (I) wherein $R_{13}$ is selected from propyl or N-propyl nitrile.

According to another aspect, is provided a pro-fluorophore of Formula (I) wherein $R_{13}$ is optionally substituted propyl.

According to a further aspect, is provided a pro-fluorophore of Formula (I) wherein $R_{16}$ is H.

According to a further aspect, is provided a pro-fluorophore of Formula (I) wherein $R_{17}$ is H.

According to a further aspect, is provided a pro-fluorophore of Formula (I) wherein $R_{17}$ is optionally substituted $C_1$-$C_6$ alkyl.

According to another further aspect, is provided a pro-fluorophore of Formula (I) wherein $R_{17}$ is ethyl.

According to another aspect, is provided a pro-fluorophore of Formula (I) wherein Z is methyl.

According to another aspect, is provided a pro-fluorophore of Formula (I) wherein Z is —C(H)(ethyl)-.

According to a one embodiment, pro-fluorophore compounds of the invention are selected from the following group:

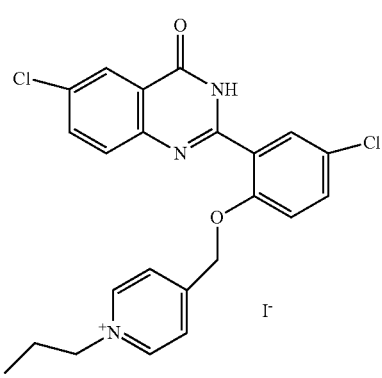

(1)

1-propyl-4-((4-chloro-2-(6-chloro-4-oxo-3,4-dihydroquinazolin-2-yl)phenoxy)methyl)pyridin-1-ium (compound (1));

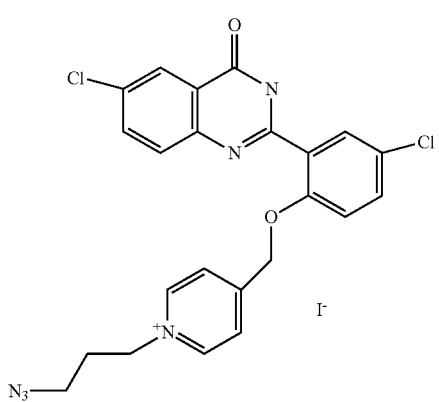

3-[4-[[4-chloro-2-(6-chloro-4-oxo-3H-quinazolin-2-yl)phenoxy]methyl]pyridin-1-ium-1-yl]propanenitrile (compound (2)) and

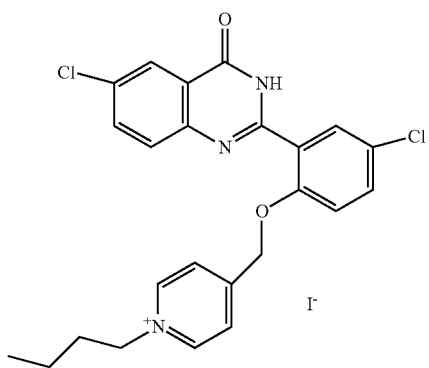

1-butyl-4-((4-chloro-2-(6-chloro-4-oxo-3,4-dihydroquinazolin-2-yl)phenoxy)methyl)pyridin-1-ium (compound (3)).

According to another embodiment, pro-fluorophore compounds of the invention are selected from the following group:

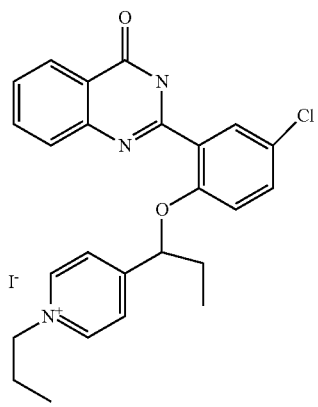 [SMILES: [I-] ; CCC[n+]1ccc(C(CC)Oc2ccc(Cl)cc2-c2nc3ccccc3c(=O)[nH]2)cc1]

4-(1-(4-chloro-2-(4-oxo-3,4-dihydroquinazolin-2-yl)phenoxy)ethyl)-1-propylpyridin-1-ium (5),

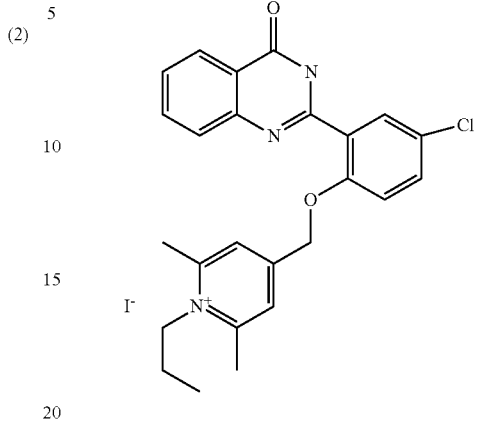

4-((4-chloro-2-(4-oxo-3,4-dihydroquinazolin-2-yl)phenoxy)methyl)-2,6-dimethyl-1-propylpyridin-1-ium (6), and

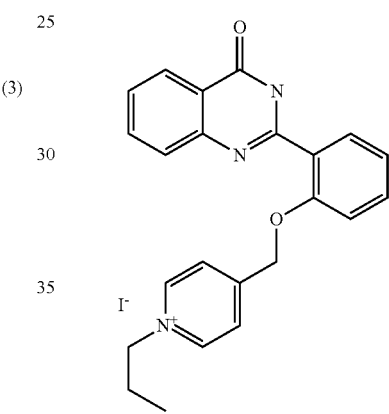

4-((2-(4-oxo-3,4-dihydroquinazolin-2-yl)phenoxy)methyl)-1-propylpyridin-1-ium (7).

According to further embodiment, a compound according to the invention is 1-propyl-4-((4-chloro-2-(6-chloro-4-oxo-3,4-dihydroquinazolin-2-yl)phenoxy)methyl)pyridin-1-ium.

According to further embodiment, a compound according to the invention is 3-[4-[[4-chloro-2-(6-chloro-4-oxo-3H-quinazolin-2-yl)phenoxy]methyl]pyridin-1-ium-1-yl]propanenitrile.

According to further embodiment, a compound according to the invention is 4-(1-(4-chloro-2-(4-oxo-3,4-dihydroquinazolin-2-yl)phenoxy)ethyl)-1-propylpyridin-1-ium.

According to another further embodiment, a compound according to the invention is 4-((4-chloro-2-(4-oxo-3,4-dihydroquinazolin-2-yl)phenoxy)methyl)-2,6-dimethyl-1-propyl pyridin-1-ium.

According to another further embodiment, a compound according to the invention is 4-((2-(4-oxo-3,4-dihydroquinazolin-2-yl)phenoxy)methyl)-1-propyl pyridin-1-ium.

According to a particular embodiment, a pro-fluorophore of the invention is colourless under visible light and soluble in aqueous solutions at room temperature.

According to another particular embodiment, a pro-fluorophore of the invention is transformed under photoredox catalytic reaction by interaction with a transition metal complex, in presence of a reducing agent, into a fluorescent compound insoluble in aqueous solutions (e.g. precipitates).

Synthesis of Pro-Fluorophores According to the Invention

According to one embodiment, pro-fluorophore compounds of the invention may be prepared by a synthetic method according to general Scheme 1 below. An aldehyde of Formula (i) in alkaline medium (e.g. potassium carbonate) was dissolved in polar solvent (e.g. DMF). The mixture was heated (e.g. 80° C.) and a pyridine derivative of Formula (iia) is added portion-wise as a solid. The resulting mixture is stirred for few hours (e.g. 6 hours). The solvent was then evaporated under reduced pressure and the residue purified by column chromatography on silica gel to afford the desired intermediate product of Formula (iii). The obtained compound of Formula (iii) is then reacted with an alkylating agent (e.g. butan-2-yl trifluoromethanesulfonate or of Formula (iv) like 1-iodopropane) in a polar aprotic solvent (e.g. DMSO) to alkylate the nitrogen atom from the pyridine under inert atmosphere. The solution is stirred overnight at room temperature. The crude is precipitated (e.g. in diethyl ether), centrifuged and washed to obtain the desired intermediate of Formula (v). The intermediate of Formula (v) is then reacted with an amide of formula (vi) in an elimination reaction (e.g. in presence of tosylic acid) in a water soluble solvent (e.g. dry ethanol) and the mixture is refluxed (e.g. 3 hours). The solution is then cooled down to 0° C. and precipitated in oxidant medium (e.g. in 2,3-dichloro-5,6-dicyano-1,4-benzoquinone (DDQ)) while the solution is let warm at room temperature. After few hours (e.g. 2 hours), compound of Formula (I) solid is recovered by centrifugation followed and washed with water soluble solvent (e.g. cold ethanol).

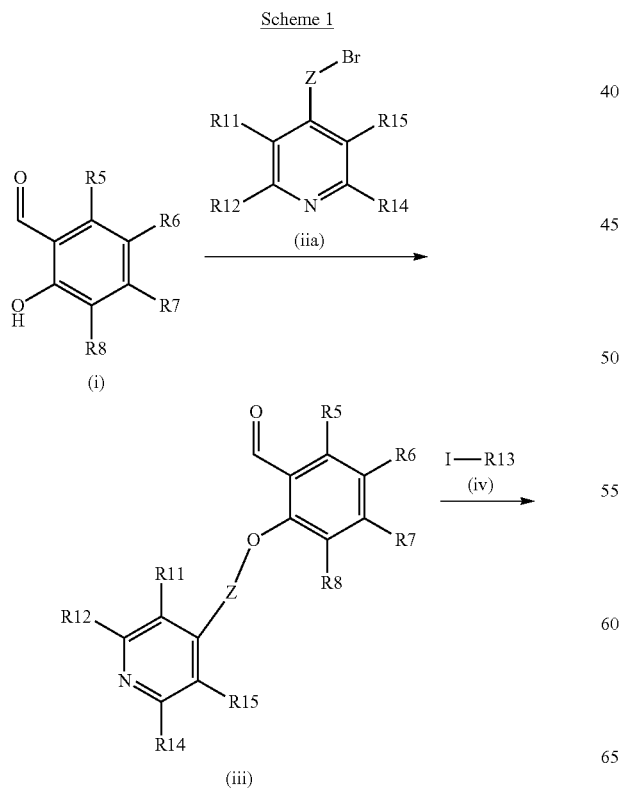

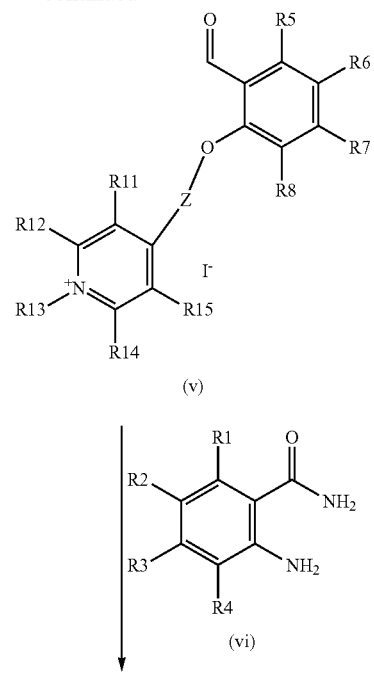

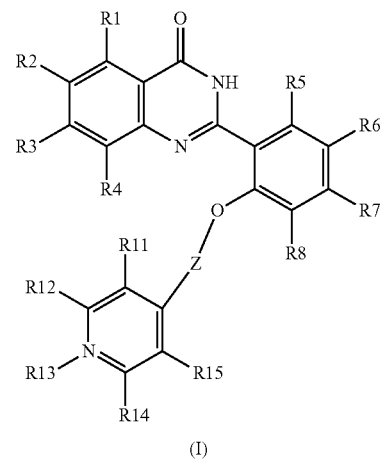

Alternatively, according to another embodiment, pro-fluorophore compounds of the invention may be prepared by a synthetic method according to general Scheme 1, wherein intermediate (iia) is replaced by intermediate (iib) and is reacted with an aldehyde of Formula (i) to prepare an intermediate (iii), according to Scheme 3 below: Scheme 3

Scheme 3

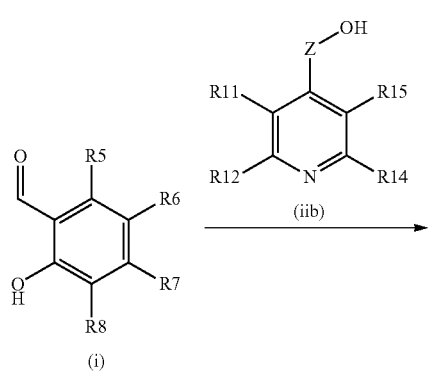

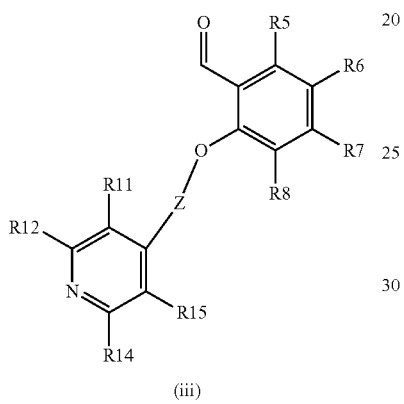

wherein intermediate (iib) is activated under standard Mitsunobu conditions (DIAD, PPh$_3$). Intermediates of Formulae (i), (iia) or (iib) might be commercially available or prepared according to standard methods known in the art.

The compound according to Formula (I) is then dissolved a polar aprotic solvent (e.g. DMSO) purified by suitable methods, such as by centrifugation and washing with cold ethanol.

It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures.

Pro-fluorophores of the invention can be used as such in solution or in the form of conjugates together with small molecules, natural or synthetic nucleic acids, peptides or proteins. For example, it can be coupled from its pyridinium group to a nucleic acid sequence such as a peptide nucleic acid (PNA) sequence, in particular via a lysine residue at the c position of the side chain or conjugated by "click" chemistry through an azide-alkyne cycloaddition by reacting an azide bearing pro-fluorophore of the invention with alkyne-bearing PNA for example as described Sadhu et al., 2013, Chem. Eur. J., 19, 8182-8189. According to a particular embodiment, conjugates of pro-fluorophores of the invention are of Formula (II):

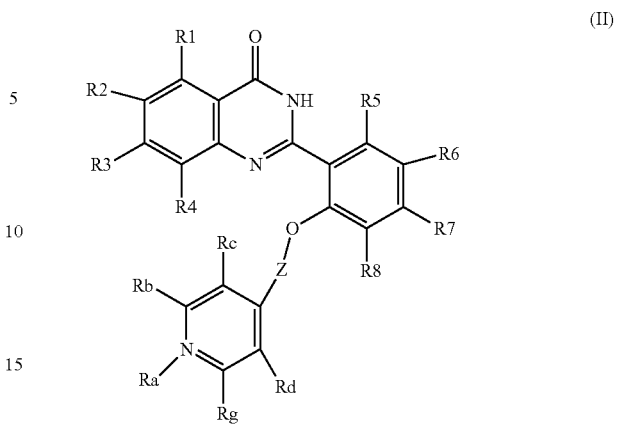

Wherein Ra is a moiety —R$_{13}$-R$_{13a}$, R$_b$ is a moiety —R$_{12}$-R$_{12b}$, R$_c$ is a moiety —R$_{11}$-R$_{11c}$, R$_d$ is a moiety —R$_{15}$-R$_{15d}$, R$_g$ is a moiety —R$_{14}$-R$_{14g}$, wherein R$_{11}$-R$_{13}$ and Z are as described herein, R$_{11c}$, R$_{12b}$, R$_{13a}$, R$_{14g}$ and R$_{15d}$ are independently optionally present and at least one of the groups R$_{11c}$, R$_{12b}$, R$_{13a}$, R$_{14g}$ and R$_{15d}$ is a linking group having a specific affinity for the target molecule (e.g. DNA, LNA, PNA, complementary to a region of the target molecule, morpholine, RNA, antibodies, nanobodies and analogues thereof or small molecule ligand), in particular in vicinity of the region which is recognized by the target probe or a group having a specific affinity for the group conjugating the photoredox catalyst to the probe recognizing a region of the target molecule (e.g. DNA, LNA, PNA, morpholine, RNA, antibodies, nanobodies and analogues thereof or small molecule ligand).

Figure 4:
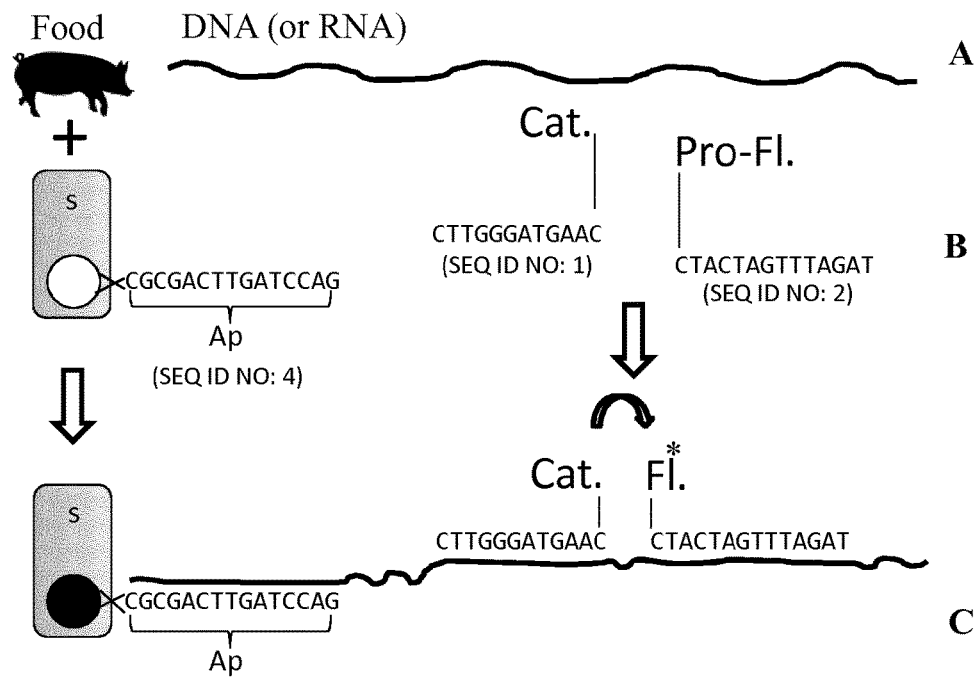
FIG. 4 illustrates a method of detection of a target pork DNA fragment in a food sample as described in Example 5. A: a food sample containing a target pork DNA fragment is provided; B: The sample is contacted with an anchoring substrate (s) bearing an anchoring probe (Ap) for said target pork DNA fragment and with a probe for the target DNA fragment labelled with a transition metal complex photoredox catalyst (Cat.) under suitable conditions for the labelled probe to bind the target molecule and the target molecule to be anchored onto the surface of the anchoring substrate through the anchoring probe, while another probe for target pork DNA fragment conjugated with a profluorophore (Pro-Fl.) of the invention is provided; C: Under suitable conditions, the probe bearing the profluorophore (Pro-Fl.) hybridizes with the anchored target molecule in the proximity of the binding site of the probe labelled with the photoredox catalyst in presence of a reducing agent and photoredox catalysis of the profluorophore into the corresponding fluorophore (Fl.) occurs.
Figure 5:
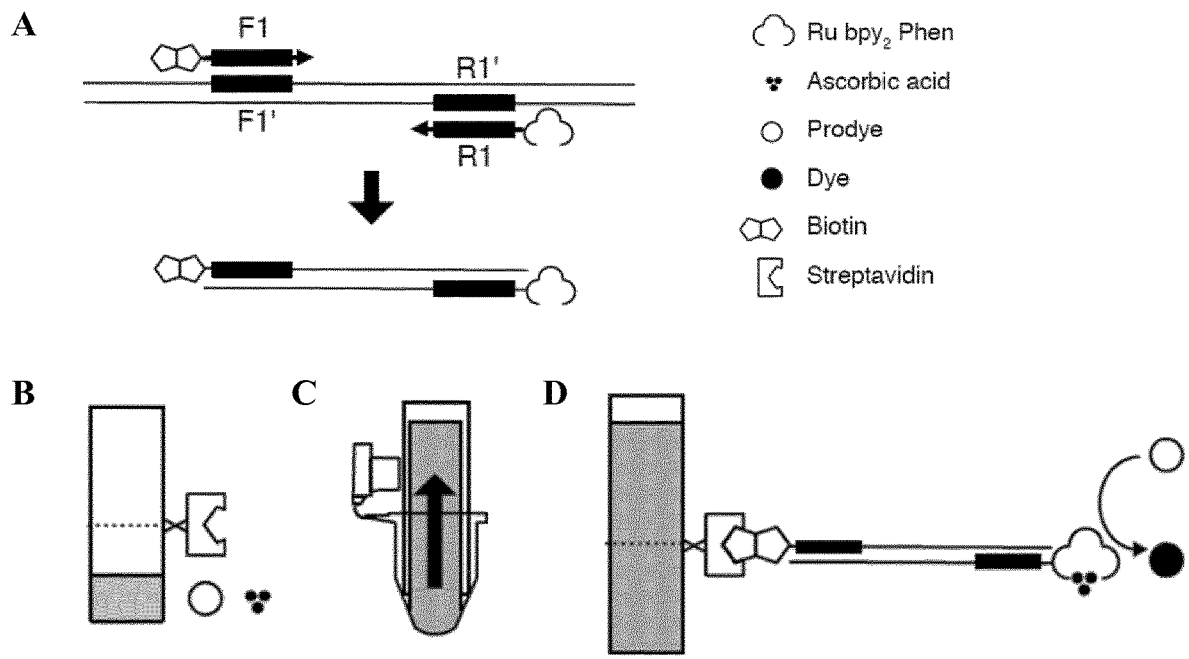
FIG. 5 schematically represents steps of a method of the invention (A-D) for detection of a target DNA fragment in a sample subjected to DNA amplification as described in Example 6.
Figure 6:
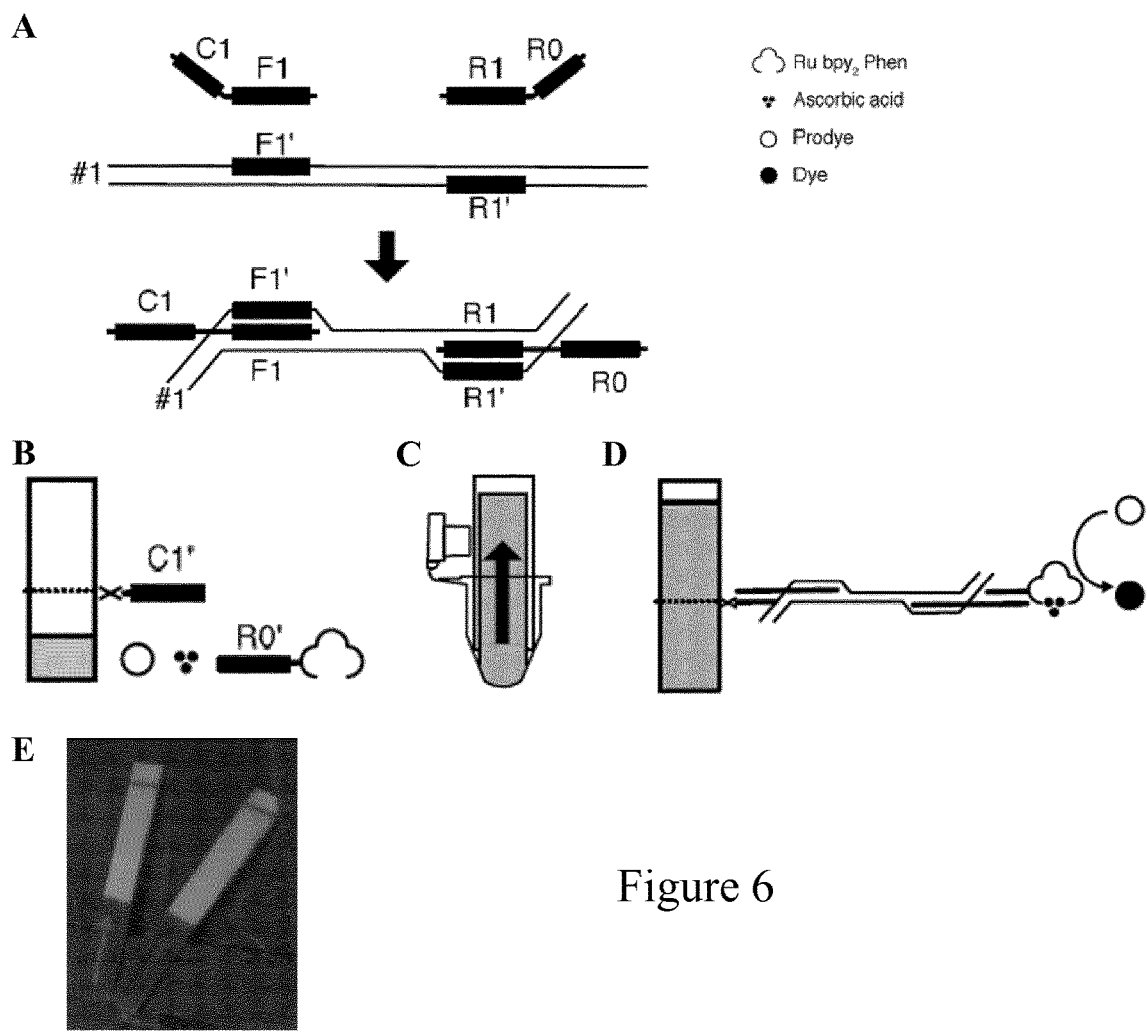
FIG. 6 schematically represents steps (A-D) and results (E) of an assay for detection of a DNA fragment in a sample by strand-invasion and DNA-templated reaction as described in Example 6.

Examples of those linking groups and conjugates and their use according to the invention are provided under FIGS. 4 and 9 and Examples 2 and 7. According to a particular embodiment compound (2) which is an azide derivative of compound (1) is particularly useful for obtaining conjugates of compound (1) according to the invention through click chemistry.

According to a particular embodiment, those linking groups having a specific affinity for the target molecule or for the group conjugating the photoredox catalyst to the probe recognizing a region of the target molecule and may comprise (a) a spacing moiety and (b) a docking moiety wherein the docking moiety (b) binds to either the target molecule in the vicinity of the region which is recognized by the catalytic probe or to the group conjugating the photoredox catalyst to the probe recognizing a region of the target probe and the spacing moiety (a) is a chemical spacer covalently linking the docking moiety to the pro-fluorophore of the invention and having an appropriate geometry to favor template reactions. According to a particular aspect, the spacing moiety can be a simple alkyl linker (typically about C$_1$-C$_{10}$ alkyl) or a polyethylene glycol or polyamide chain, typically of about 1-10 units (0.3-3 nm).

According to a particular embodiment, conjugates of pro-fluorophores of the invention are of Formula (II) wherein at least one $R_{11c}$, $R_{12b}$, $R_{13a}$, $R_{14g}$ and $R_{15d}$ groups is a linking group of the following Formula (III):

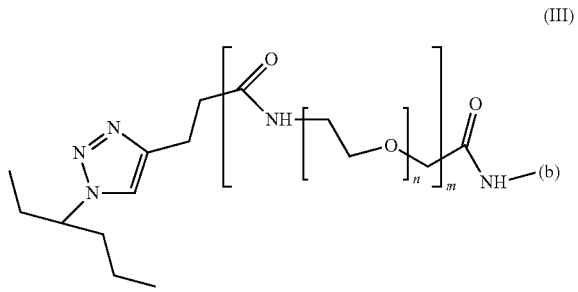

(III)

Wherein n is an integer from 1 to 10, m is an integer from 0 to 2 and b is a docking moiety as defined above.

According to a further particular embodiment, conjugates of pro-fluorophores of the invention are of those described in the Examples.

Photocatalytic Reduction of Pro-Fluorophores of the Invention

According to one aspect, a pro-fluorophore of Formula (I) can be used as a fluorogenic composition (fluorophore precursor) for a photoredox catalysis occurring when the pro-fluorophore of Formula (I) is in the vicinity of a transition metal complex photoredox catalyst.

According to particular aspect, a photoredox catalyst can be selected from known transition metals such as described in Prier et al., 2013, *Chem. Rev.*, 113, 5322-5363.

In particular, a photoredox catalysis (photocatalytic reduction) can be mediated by a transition metal complex (photoredox catalyst) of Formula (I"):

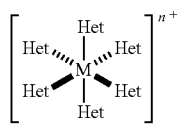

(I")

wherein M is a transition metal (such as Ruthenium), n is an integer from 1 to 6 (such as 3), Het is an optionally substituted heterocycle containing at least one Nitrogen and two Het groups may be linked by a covalent bond (such as bipyridine(bpy)) or fused (such as phenathroline (Phen)) in presence of a reducing agent when the pro-fluorophore of Formula (I) is in the vicinity of the said photoredox catalyst such that the said photoredox catalyst is able to engage in a single-electron transfer process with a fluorogenic composition comprising said pro-fluorophore of Formula (I) are upon excitation with light.

According to a particular aspect, M is Ruthenium (Ru).

According to another particular aspect, Het is selected from optionally substituted bipyridine (bpy) (such as bipyridine or chloro bipyridine) and phenathroline (Phen).

According to a further particular aspect, a photoredox catalyst useful to trigger the photoredox catalysis of a fluorogenic composition comprising a pro-fluorophore of Formula (I) is selected from tris(bipyridine)ruthenium(II) chloride ($Ru(bpy)_3Cl_2$), bis(bipyridine) ruthenium(II) phenanthro line ($Ru(bpy)_2Phen$) or related analogues.

According to a particular aspect, a reducing agent can be selected from those described in Sadhu et al., 2015, *Chem. Commun.*, 51, 1664-6).

According to a further particular aspect, a reducing agent can be selected from sodium ascorbate (NaAsc), ascorbic acid and (Vitamin C), Phosphines like tris(2-carboxyethyl) phosphine, tertiary amine (ethylenediaminetetraacetic acid (EDTA) or triethanolamine) and nicotinamide adenine dinucleotide (NADH).

According to another further particular aspect, a reducing agent is a sodium ascorbate (NaAsc).

Among quinazolinone precipitating dyes, 6-chloro-2-(5-chloro-2-hydroxy-phenyl)-3H-quinazolin-4-one is one of the most known but some other fluorophores are known to behave similarly (Diwu et al., 1999, *Conference on Advances in Fluorescence Sensing Technology IV, SPIE*, 3602) and some further ones have been shown to behave similarly, as illustrated in Example 9. Therefore, the method of the invention is useful in the preparation of various QPD of interest, in particular for use in the detection of target molecules.

According to another aspect, is provided a method of preparation of a fluorophore of Formula (I'):

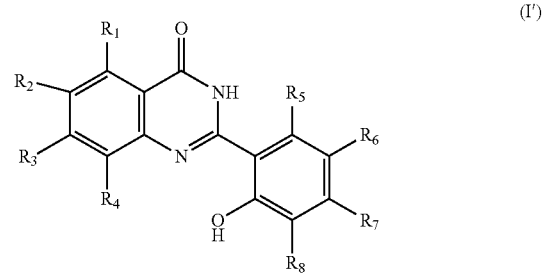

(I')

wherein $R^1$ to $R^8$ are independently selected from hydrogen, hydroxyl, halogen such as chloro, cyano, nitro, optionally substituted $C_1$-$C_{10}$ alkyl, optionally substituted amino $C_1$-$C_{10}$ alkyl, optionally substituted $C_1$-$C_{10}$ alkoxy, or any tautomer, isomer, conjugate or salts thereof, comprising a step of reacting a fluorogenic composition comprising a pro-fluorophore of Formula (I) as defined herein with a transition metal complex photoredox catalyst, in presence of a reducing agent through a photoredox catalysis.

According to another aspect, is provided a method of preparation of a fluorophore of Formula (I'), wherein $R_1$, $R_3$ to $R_5$ and $R_7$ to $R_8$ are H.

According to another aspect, is provided a method of preparation of a fluorophore of Formula (I'), wherein $R_2$ is Cl.

According to another aspect, is provided a method of preparation of a fluorophore of Formula (I'), wherein $R_2$ is H.

According to another aspect, is provided a method of preparation of a fluorophore of Formula (I'), wherein $R_6$ is Cl.

According to another aspect, is provided a method of preparation of a fluorophore of Formula (I'), wherein $R_6$ is H.

According to another aspect, is provided a method of preparation of a fluorophore of Formula (I'), wherein $R_6$ is optionally substituted $C_1$-$C_{10}$ alkyl.

According to a further embodiment aspect, is provided a method of preparation of a fluorophore of Formula (I'), wherein $R_6$ is alkoxycarbonyl $C_1$-$C_{10}$ alkyl such as —$CH_2C(O)OMe$.

According to another aspect, is provided a method of preparation of a fluorophore of Formula (I'), wherein $R_1$-$R_8$ are H.

According to another aspect, is provided a method of preparation of the fluorophore:

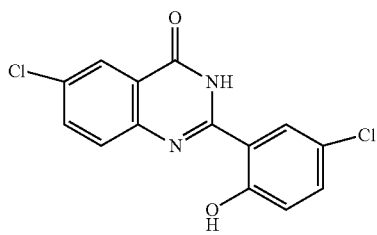 [SMILES: O=c1[nH]c(-c2cc(Cl)ccc2O)nc2ccc(Cl)cc12]

6-chloro-2-(5-chloro-2-hydroxy-phenyl)-3H-quinazolin-4-one (8).

According to another aspect, is provided a method of preparation of a fluorophore selected from the following group:

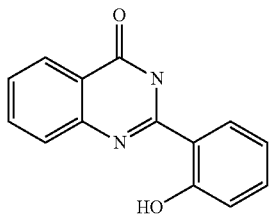 [SMILES: O=c1[nH]c(-c2ccccc2O)nc2ccccc12]

2-(2-hydroxyphenyl)quinazolin-4(3H)-one (9);

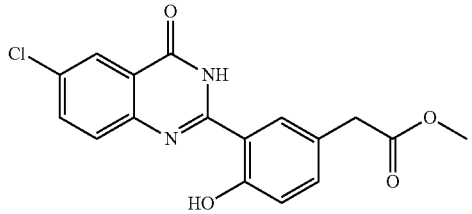

methyl 2-(3-(6-chloro-4-oxo-3,4-dihydroquinazolin-2-yl)-4-hydroxyphenyl)acetate (10); and

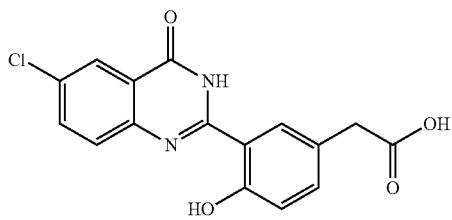 [SMILES: O=C(O)Cc1ccc(O)c(-c2nc3ccc(Cl)cc3c(=O)[nH]2)c1]

2-(3-(6-chloro-4-oxo-3,4-dihydroquinazolin-2-yl)-4-hydroxy phenyl)acetic acid (11).

According to another aspect, is provided a fluorophore selected from the following group:

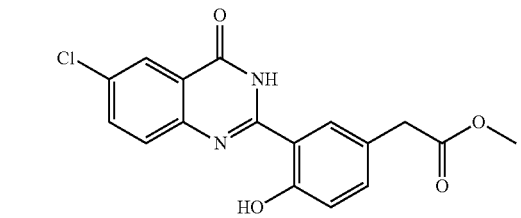 [SMILES: COC(=O)Cc1ccc(O)c(-c2nc3ccc(Cl)cc3c(=O)[nH]2)c1]

methyl 2-(3-(6-chloro-4-oxo-3,4-dihydroquinazolin-2-yl)-4-hydroxyphenyl)acetate (10); and

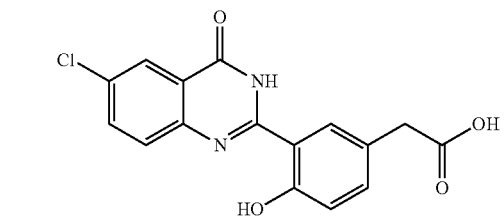 [SMILES: O=C(O)Cc1ccc(O)c(-c2nc3ccc(Cl)cc3c(=O)[nH]2)c1]

2-(3-(6-chloro-4-oxo-3,4-dihydroquinazolin-2-yl)-4-hydroxy phenyl)acetic acid (11).

According to a particular aspect, the photoredox catalysis is initiated by a radiation of a wavelength sufficient to excite the metal to ligand transition, typically between about 400 to about 500 nm, in particular between about 430 to about 470 nm, in particular between about 450 (e.g. for Ru(bpy)$_3$ or Ru(bpy)$_2$Phe) to about 460 nm.

According to a particular aspect, the photoredox catalysis is initiated by a radiation of a wavelength of about 450-455 nm.

According to a particular embodiment, the method of preparation of the fluorophore is conducted on a solid support on which the target molecule bearing the transition metal complex photoredox catalyst is bound to.

According to another particular embodiment, the fluorophore is formed by a method of preparation of the fluorophore according to the invention and precipitates at the site of the reaction between the transition metal complex photoredox catalyst and the fluorogenic composition comprising a pro-fluorophore of Formula (I). Thus, the catalyst is enriched at a given physical location on a solid support where the target molecule (analyte) is present and the formation of the fluorophore leads to a fluorescent precipitate, the fluorescence signal intensity correlating with the concentration of the target DNA conjugated to the catalyst.

According to another aspect, is provided a method for the detection of at least one target molecule (e.g. small molecule, natural and synthetic nucleic acid, peptide or protein) in a sample comprising a step of detecting a fluorophore of Formula (I') formed according to a method of the invention.

The detection of the formation of a fluorophore of Formula (I') can be achieved with unaided eye or can visualized by a radiation of wavelength between about 300 to about 400 nm, in particular between about 330 to about 380 nm, in particular between about 360 to about 370 nm, such as under a black light (e.g. 365 nm UV lamp).

Methods and Uses According to the Invention

A pro-fluorophore of Formula (I) or a conjugate thereof according to the invention can be used as a fluorogenic composition (fluorophore precursor) for a photoredox catalysis occurring when the pro-fluorophore of Formula (I) is in the vicinity of a transition metal complex photoredox catalyst.

In particular, a pro-fluorophore of Formula (I) or a conjugate thereof according to the invention can be used in a method for the detection of at least one target molecule (e.g. small molecule, natural and synthetic nucleic acid, peptide or protein) in a sample, wherein said method comprises:

(i) Contacting a sample with (1) an anchoring substrate for said at least one target molecule and (2) with a probe for said at least one target molecule, wherein said probe is labelled with a transition metal complex photoredox catalyst, under suitable conditions for the probe to bind the said at least one target molecule and for the target molecule to be anchored onto (e.g. the surface of) the said anchoring substrate if the said target molecule is present in the sample;

(ii) Contacting a composition comprising a pro-fluorophore according to the invention or a conjugate thereof with the said anchoring substrate, in presence of a reducing agent under suitable condition for inducing a photoredox catalysis of the pro-fluorophore according to the invention or a conjugate thereof when the pro-fluorophore is located the vicinity of the transition metal complex photoredox catalyst;

(iii) Detecting the formation of a fluorophore of Formula (I') on said anchoring substrate, wherein the formation of said fluorophore is indicative of the presence of the said at least one target molecule within said sample.

In a particular embodiment, is provided a method of the invention for the detection of at least one target molecule in a sample, wherein said method further comprises a step (ia) of washing the said anchoring substrate before carrying out step (ii) to remove any molecule unbound to said anchoring substrate.

In a particular aspect, is provided a method of the invention for the detection of at least one target molecule in a sample wherein said steps (i) and (ii) are achieved in parallel through the use of a profluorophore conjugate of the invention in which said profluorophore is conjugated to a probe that specifically recognizes (e.g. through Watson/Crick nucleobase pairings) a portion of a sequence of a target nucleic acid (e.g. DNA) sequence ("profluorophore probe") and the use of a probe for said at least one target molecule, wherein said probe is labelled with a transition metal complex photoredox catalyst ("catalytic probe"). In this variant, the profluorophore conjugate itself serves as an anchoring substrate for the target nucleic acid for the photocatalytic reaction to occur once the catalytic probe also binds to the target nucleic acid.

Therefore, according to another particular aspect of the invention, a method for the detection of at least one target molecule (e.g. small molecule, natural and synthetic nucleic acid, peptide or protein) in a sample, wherein said method comprises:

(ia) Contacting a sample with (1) a probe for said at least one target molecule, wherein said probe is labelled with a profluorophore according to the invention or a conjugate thereof ("profluorophore probe") and (2) with a probe for said at least one target molecule, wherein said probe is labelled with a transition metal complex photoredox catalyst, in presence of a reducing agent and under suitable conditions for the probes to bind the said at least one target molecule, if the said target molecule is present in the sample, under suitable condition for inducing a photoredox catalysis of the pro-fluorophore according to the invention or a conjugate thereof when the pro-fluorophore conjugate is bound on the target molecule in the vicinity of the transition metal complex photoredox catalyst;

(ib) Detecting the formation of a fluorophore of Formula (I'), wherein the formation of said fluorophore is indicative of the presence of the said at least one target molecule within said sample.

This particular variant advantageously allows the use of a method of the invention without the need of a physical anchoring though a support substrate for applications in which the target nucleic acid is very abundant and without the need of washing step. In fact, since without target nucleic acid photoredox catalysis will occur slowly and randomly between free catalytic and profluorophore probes and therefore the color change due to the formation of the fluorophore when the target nucleic acid is present will be observable.

In a particular embodiment, is provided a method of the invention for the detection of at least one target molecule in a sample wherein said at least one target molecule is a nucleic acid sequence or a portion of a target nucleic acid sequence.

In a particular embodiment, is provided a method of the invention for the detection of at least one target molecule in a sample wherein said at least one target molecule is a target DNA sequence or a portion of a target DNA sequence.

In a particular embodiment, is provided a method of the invention for the detection of at least one target molecule in a sample wherein said at least one target molecule is a target RNA sequence or a portion of a target RNA sequence.

In a particular embodiment, is provided a method of the invention for the detection of at least one target molecule in a sample wherein said probe for said at least one target molecule labelled with a transition metal complex photoredox catalyst is a nucleic acid probe for a target nucleic acid sequence or a portion of a target nucleic acid sequence labelled with a transition metal complex photoredox catalyst, for example it can be a nucleic acid "Velcro" probe that specifically recognize a portion of a sequence of a target nucleic acid sequence through Watson/Crick nucleobase pairings, wherein said probe is labelled with a transition metal complex photoredox catalyst. Examples of nucleic acid "velcros" are RNAs, DNAs, PNAs or LNAs as described in Briones et al. (2012, Anal. Bioanal. Chem., 402(10): 3071-89) or mixtures thereof. Nucleic acid probe for a target nucleic acid sequence or a portion of a target nucleic acid sequence labelled with a transition metal complex photoredox catalyst can be a γD-PNA, γL-PNA In a particular embodiment, is provided a method of the invention for the detection of at least one target molecule in a sample wherein said anchoring substrate is a substrate such as a test strip (such as cellulose esters (including nitrocellulose acetate, and cellulose acetate), cellulosic paper, filter paper, tissue paper, or other porous polymer film), containing an agent that allows the target molecule to be anchored onto the surface of said substrate. For example, an anchoring substrate can be a substrate comprising a "Velcro" probe for said target nucleic acid (e.g. DNA) sequence or a portion of said target DNA sequence immobilized on streptavidin-agarose beads, a substrate comprising a streptavidin group, a substrate comprising antibodies or nanobodies against common (nucleic acid (e.g. DNA) markers (such as fluorescein isothiocyanate, digoxigenine, dinitrophenyl and biotin).

Examples of the method of detection of at least one target nucleic acid (e.g. DNA) molecule in a sample according to the invention are illustrated on FIGS. 1, 2, 4 to 9.

In a particular embodiment, is provided a method of the invention for the detection of at least one target molecule in a sample wherein said step (i) is achieved through the use of at least two different types of probes such as (a) a probe that specifically recognizes (e.g. through Watson/Crick nucleobase pairings) a portion of a sequence of a target nucleic acid (e.g. DNA) sequence (or a complementary sequence to a sequence covalently linked to a sequence string that recognizes the target molecule) and ensuring the anchoring of the target molecule on the substrate ("anchoring probe") and (b) a probe that specifically recognizes (e.g. through Watson/Crick nucleobase pairings) a portion of a sequence of a target nucleic acid (e.g. DNA) sequence (or a complementary sequence to a sequence covalently linked to a sequence string that recognizes the target molecule) labelled with a transition metal complex photoredox catalyst ("catalytic probe").

In one embodiment, is provided a method of the invention for the detection of at least one target molecule in a sample wherein said step (i) is achieved through the use of at least two probes that are specific to and hybridize on the same target DNA molecule.

In a particular embodiment, is provided a method of the invention for the detection of at least one target molecule in a sample wherein step (i) comprises a step of DNA amplification using probes (primers) conjugated to the anchoring group (anchoring probe) and (primers) conjugated to the photoredox catalyst (catalytic probe) leading after DNA amplification to a target DNA molecule comprising a molecule for immobilisation on the anchoring substrate and a photoredox catalyst.

In another particular embodiment, is provided a method of the invention for the detection of at least one target molecule in a sample wherein the anchoring probe is selected from a biotinylated DNA sequence that specifically recognizes (e.g. through Watson/Crick nucleobase pairings) a portion of a sequence of a target DNA sequence (or a complementary sequence to a sequence covalently linked to a sequence string that recognizes the target molecule) which is able to anchor to the streptavidin groups of the anchoring substrate under step (i) or a probe that specifically recognizes (e.g. through Watson/Crick nucleobase pairings) a portion of a sequence of a target DNA sequence (or a complementary sequence to a sequence covalently linked to a sequence string that recognizes the target molecule) already anchored to the anchoring substrate.

In another particular embodiment, is provided a method of the invention for the detection of at least one target molecule in a sample wherein step (ii) is achieved through the use of a fluorogenic composition comprising a conjugate of a profluorophore of the invention, wherein said conjugate comprises a nucleic acid (e.g. DNA) sequence that specifically recognizes a region of the target molecule in the vicinity of the region recognized by the catalytic probe or a nucleic acid (e.g. DNA) sequence that specifically recognizes, within the catalytic probe, a linker conjugating the catalyst to the probe specifically recognizing a region of the target molecule.

Probe Molecules

According to one aspect, the invention provides a probe that recognizes and binds to a specific nucleic acid target sequence.

According to one aspect, the invention provides a conjugate comprising a DNA probe that recognizes and binds to a specific target DNA region such as a DNA mini-barcode or to a nucleic acid of another probe (RNA, DNA, PNA or LNA) conjugated to a compound of Formula (I).

In some instances, the photocatalytic reaction can be further accelerated using nucleic acid overhang to template the catalyzed profluorophore conversion and the assay can be multiplexed by assigning specific immobilization sequences (barcode). In order to avoid cross-talk between the overhang sequence and analyte-binding sequences, two different stereochemistries of PNA are used (L-gamma PNA for DNA or RNA targeting sequence and R-gamma PNA for templated reaction and immobilization). Such procedure is illustrated in Example 7.

A particular advantage of a method of the invention is that, contrarily to standard DNA detection techniques, it does not necessitate laboratory setting and thus the use of any instruments, toxic reagents or complex procedures like bioinformatics analysis. The present invention is thus a cost-effective analysis that can be performed and interpreted by anyone without a prior knowledge on DNA detection tests, it is portable and disposable and can be performed within short time (minutes or seconds). Therefore, the present invention is particularly useful for detection of target molecules, in particular, specific target DNAs in a complex sample mixture such as in food (e.g. for detection of allergic ingredients), organic fluids (e.g. for point-of-care diagnostics of viruses or bacteria), environmental samples (e.g. for biodefense or hygiene testing) and otherwise difficult to identify samples (e.g. specimens from endangered wildlife). The present invention is also useful for traceability purposes, as it can provide a point-of-need authentication tool for products in which naturally occurring or artificially introduced DNAs are used as tracers or watermarks (e.g. textiles, watches, cigarette filters etc.).

Test Device

A test device particularly useful for use in a method of the invention comprises an anchoring substrate that allows migration of the reactants by capillarity and that allows the binding to target molecules or probes of the invention, for example such as described in U.S. Pat. No. 5,798,273.

In one aspect, a test device comprises an anchoring substrate comprising a material selected from cellulose esters (including nitrocellulose acetate, and cellulose acetate), cellulosic paper, filter paper, tissue paper, or porous polymer film.

In another aspect, the anchoring substrate comprises at its surface a capture probe (e.g. streptavidin or anchored probes) that allows the binding to target molecules or probes of the invention.

Kits

Another aspect of the invention provides a kit for the detection of at least one target molecule in a sample, said kit comprising a pro-fluorophore of Formula (I) or a conjugate thereof and, optionally, at least one agent selected among a reducing agent and a further probe for the detection of said target molecule. According to a particular aspect, the kit further comprises a test device according to the invention.

According to a more particular aspect, a kit according to the invention comprises at least one catalytic probe and one anchoring probe having a specific affinity for the target molecule (e.g. lyophilized probes), a reducing agent and a pro-fluorophore according to the invention, optionally together with at least one vessel for conducting amplification reaction and/or a sampling device.

According to a more particular aspect, a kit according to the invention comprises at least one catalytic probe and one anchoring probe having a specific affinity for the target molecule (e.g. lyophilized probes), a reducing agent and a pro-fluorophore according to the invention, optionally together with at least one target molecule whose positive detection can be used as control.

According to another further aspect, is provided a kit according to the invention comprises at least one catalytic probe and one anchoring probe having a specific affinity for the target molecule (e.g. lyophilized probes) and a strip device with a detection line made of immobilized streptavidin and a bottom pouch containing a mixture of a pro-fluorophore according to the invention and a reducing agent.

EXAMPLES

The following abbreviations refer respectively to the definitions below:
bp (base pair), COI (cytochrome c oxidase), DDQ (2,3-dichloro-5,6-dicyano-1,4-benzoquinone), DIAD (Diisopropyl azodicarboxylate), DMF (dimethylformamide), DMSO (dimethyl sulfoxide), dsDNA (double stranded DNA), EtOH (ethanol), LED (light-emitting diode), LNA (locked nucleic acids), PBS (phosphate-buffered saline), m-CPBA (meta-chloroperoxybenzoic acid), PNA (peptide nucleic acid), TsOH (tosylic acid), MS (ESI) (mass spectrometry (electrospray ionization)), NaAsc (sodium ascorbate), NMR (nuclear magnetic resonance), QR™ code (Quick Response Code), RP-HPLC (reversed-phase high-performance liquid chromatography), Ru(bpy)$_3$Cl$_2$ (tris(bipyridine)ruthenium (II) chloride), Ru(bpy)$_2$Phen (bis(bipyridine)ruthenium(II) phenanthroline (Ru(bpy)2Phen).

Example 1: Synthesis of Pro-Fluorophores of the Invention

Pro-fluorophores of the invention can be synthesized according to general Scheme 1. The following pro-fluorophores have been synthesized according to the following procedure of Scheme 2 wherein R is selected from H (intermediates (iva), (va) and compound (1)) and N$_3$ (intermediates (ivb), (vb) and compound (2)).

Step 1—Formation of Intermediate (iiia)

5-chloro salicylaldehyde (491 mg, 3.13 mmol) (intermediate (ia)) and potassium carbonate (K$_2$CO$_3$, 1306 mg, 9.4 mmol) were dissolved in 8 ml of dimethylformamide (DMF). The mixture was heated to 80° C. and 4-(bromomethyl)pyridine hydrobromide (intermediate (iia)(800 mg, 3.13 mmol) was added portion-wise as a solid. The resulting mixture was stirred for 6 hours. The solvent was then evaporated under reduced pressure and the residue purified by column chromatography on silica gel to afford 365 mg of the desired intermediate product (iii) as a yellow solid. Yield: 47%. $^1$H NMR (nuclear magnetic resonance) (400 MHz, CDCl$_3$) δ: 10.54 (s, 1H), 8.69 (d, J=6.1 Hz, 2H), 7.86 (d, J=2.8 Hz, 1H), 7.51 (dd, J=8.9, 2.8 Hz, 1H), 7.38 (d, J=6.1 Hz, 2H), 6.96 (d, J=8.9 Hz, 1H), 5.24 (s, 2H). $^{13}$C NMR (101 MHz, CDCl$_3$) δ: 187.82, 158.64, 150.27, 144.64, 135.41, 128.51, 127.29, 126.05, 121.28, 114.38, 68.97. Mass spectrometry (electrospray ionization) (MS (ESI)): calculated for C$_{13}$H$_{10}$ClNO$_2$: 247.04, found: 248.01 [M+H]$^+$.

Scheme 2

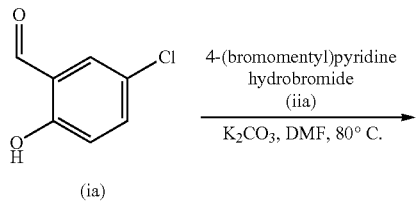

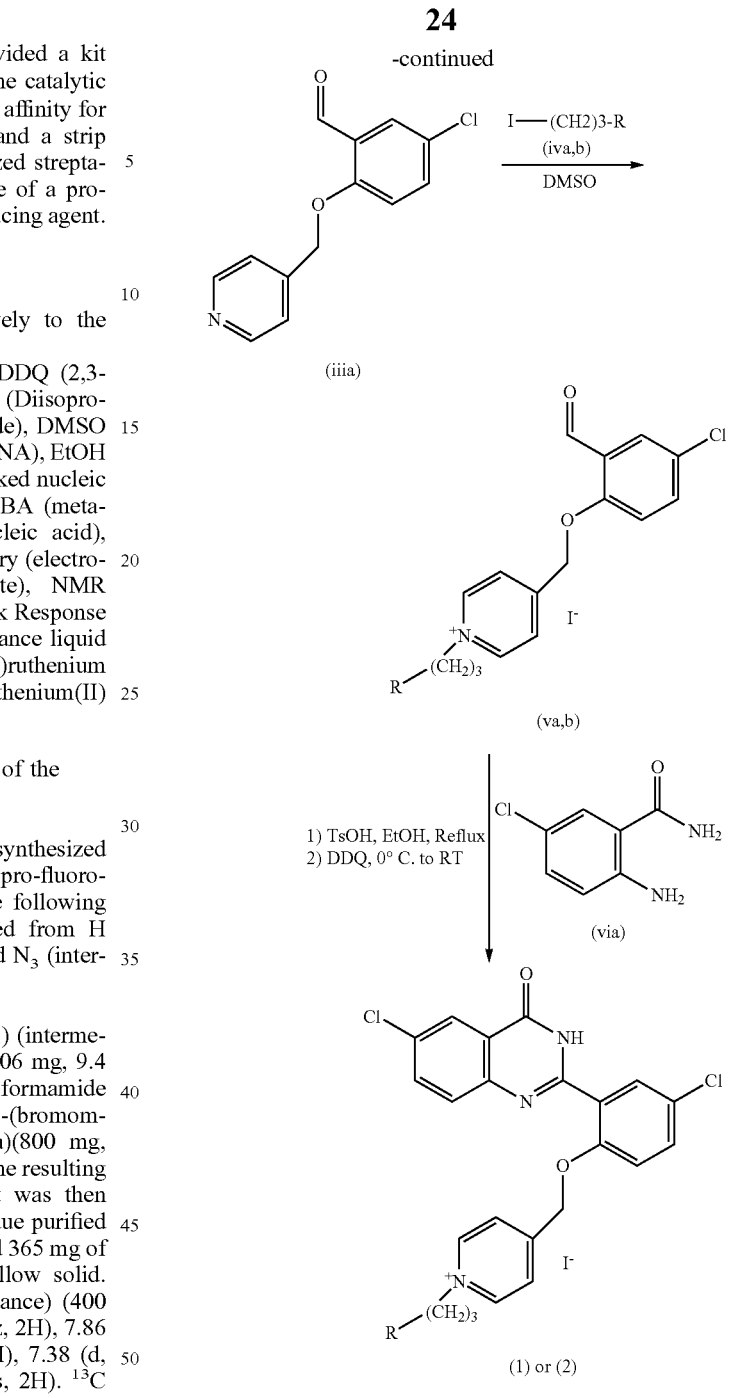

Step 2a—Formation of Intermediate (va)

Intermediate (iiia) (279 mg, 1.13 mmol) was mixed to a solution of 1-iodopropane (intermediate (iva) (3.78 g, 18 mmol) into 2.2 ml of DMSO under inert atmosphere. The solution was stirred overnight at room temperature. The crude was precipitated in diethyl ether, centrifuged and washed three times to obtain intermediate product (va) as brown oil.

Yield: 90% $^1$H NMR (400 MHz, DMSO-d$_6$) δ: 9.09 (d, J=6.8 Hz, 1H), 8.29 (d, J=6.4 Hz, 1H), 7.83-7.70 (m, 1H), 7.35 (dd, J=8.6, 0.7 Hz, 1H), 5.68 (s, 1H), 4.59 (t, J=7.3 Hz, 1H), 1.96 (q, J=7.3 Hz, 1H), 0.90 (t, J=7.4 Hz, 2H). $^{13}$C NMR (101 MHz, DMSO-d$_6$) δ: 189.03, 158.38, 156.33, 145.07, 136.07, 128.38, 126.40, 126.22, 125.55, 116.59, 68.33, 62.19, 24.57, 10.70. MS (ESI): calculated for $C_{16}H_{17}ClNO_2+$: 290.09, found: 290.17 $[M]^+$.

Step 2b—Formation of Intermediate (vb)

Intermediate product (vb) was prepared from intermediate (iiia) (365 mg, 1.47 mmol) and 1-azido-3-iodopropane (intermediate (ivb) (1.58 g, 7 mmol) as described for intermediate (va).

Yield: 75%. $^1$H NMR (400 MHz, DMSO-$d_6$) δ: 10.48 (s, OH), 9.11 (d, J=6.7 Hz, 1H), 8.30 (d, J=6.4 Hz, 1H), 7.80-7.74 (m, 1H), 7.34 (d, J=8.8 Hz, OH), 5.69 (s, 1H), 4.69 (t, J=7.2 Hz, 1H), 3.50 (t, J=6.5 Hz, 1H), 2.32-2.13 (m, 1H). $^{13}$C NMR (101 MHz, DMSO-$d_6$) δ: 189.01, 158.36, 156.47, 145.31, 136.05, 128.36, 126.40, 126.22, 125.57, 116.61, 68.33, 58.65, 48.07, 30.13. MS (ESI): calculated for $C_{16}H_{16}ClN_4O_2+$: 331.10, found: 331.10 $[M]^+$.

Step 3a—Formation of Compound (1) of the Invention

Compound (1) (114.5 mg, 0.27 mmol), 2-amino-5-chloro benzamide (intermediate (via) (49 mg, 0.29 mmol) and TsOH*$H_2O$ (11 mg, 0.06 mmol) were dissolved in 3 ml of dry ethanol (EtOH) and the mixture refluxed for 3 hours. The solution was then cooled down to 0° C. and 2,3-dichloro-5,6-dicyano-1,4-benzoquinone (DDQ) (80 mg, 0.35 mmol) was added and the solution let warm to room temperature. After 2 hours the solid was recovered by centrifugation followed and washed three times with cold ethanol. The gummy brown precipitate obtained was purified by reversed-phase high-performance liquid chromatography (RP-HPLC) to lead to compound (1). $^1$H NMR (400 MHz, DMSO-$d_6$) δ: 12.69 (s, 1H), 9.07 (d, J=6.4 Hz, 2H), 8.17-8.09 (m, 3H), 7.91 (dd, J=8.7, 2.5 Hz, 1H), 7.80 (d, J=8.7 Hz, 1H), 7.77 (d, J=2.7 Hz, 1H), 7.66 (dd, J=8.9, 2.7 Hz, 1H), 7.27 (d, J=8.9 Hz, 1H), 5.59 (s, 2H), 4.54 (t, J=7.3 Hz, 2H), 1.92 (q, J=7.3 Hz, 2H), 0.87 (t, J=7.3 Hz, 3H). $^{13}$C NMR (101 MHz, CDCl$_3$) δ: 156.75, 154.50, 151.73, 144.99, 135.18, 132.33, 131.69, 130.84, 130.22, 129.74, 125.81, 125.36, 125.28, 125.24, 122.95, 115.59, 68.48, 62.14, 24.53, 10.66. MS (ESI): calculated for $C_{23}H_{20}Cl_2N_3O_2+$: 440.09, found: 440.28 $[M]^+$.

Step 3b—Formation of Compound (2) of the Invention

Compound (2) was prepared from compound (va) (580 mg, 1.32 mmol) and 2-amino-5-chloro benzamide (270 mg, 1.4 mmol) as described for compound (1). $^1$H NMR (500 MHz, DMSO-$d_6$) δ: 12.71 (s, 1H), 9.08 (d, J=6.8 Hz, 2H), 8.17-8.09 (m, 3H), 7.92 (dd, J=8.7, 2.5 Hz, 1H), 7.81 (d, J=8.7 Hz, 1H), 7.77 (d, J=2.7 Hz, 1H), 7.67 (dd, J=8.9, 2.7 Hz, 1H), 7.27 (d, J=9.0 Hz, 1H), 5.59 (s, 2H), 4.64 (t, J=7.2 Hz, 2H), 3.47 (t, J=6.5 Hz, 2H), 2.19 (p, J=6.8 Hz, 2H). $^{13}$C NMR (126 MHz, DMSO-$d_6$) δ: 160.43, 157.72, 157.48, 156.41, 154.00, 151.24, 147.57, 144.76, 134.71, 131.82, 131.22, 130.35, 129.76, 125.33, 124.88, 124.81, 124.77, 122.48, 115.08, 67.97, 58.13, 47.57, 29.60. MS (ESI): calculated for $C_{23}H_{19}Cl_2N_6O_2+$: 481.09, found: 481.31 $[M]^+$.

Compound (3) was prepared from (iiia) according to the same procedure using iodobutane rather than iodopropane in step 2.

Further pro-fluorophores of the invention were synthesized according to general Scheme 1 wherein intermediate (iia) is replaced by an intermediate (iib) which is reacted with an aldehyde of Formula (i) to prepare an intermediate (iii), according to general Scheme 3 as follows:

Step 1—Formation of Intermediate (iib1)

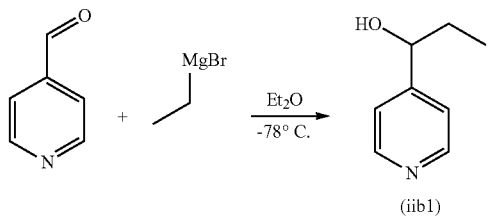

4-Pyridinecarboxaldehyde (940 μL, 10 mmol) was added dropwise to a cold solution of ethylmagnesiumbromide in diethyl ether (0.3M final concentration, 12 mmol). After the addition, the cooling bath is removed and the solution stirred at room temperature for 1 hour. The reaction was quenched with water and the crude was absorbed on silica. Purification on silica gel afforded 850 mg of an intermediate product (iib1) as a yellow viscous oil. Yield: 62%. $^1$H NMR (400 MHz, Chloroform-d) δ: 8.56 (d, J=6.1 Hz, 2H), 7.29 (d, J=5.4 Hz, 2H), 4.66 (t, J=6.3 Hz, 1H), 3.50 (s, 1H), 1.79 (qd, J=7.4, 6.2 Hz, 2H), 0.97 (t, J=7.4 Hz, 3H). $^{13}$C NMR (101 MHz, Chloroform-d) δ: 154.00, 149.45, 121.04, 74.03, 31.74, 9.72.

Step 2—Formation of Intermediate (iiib)

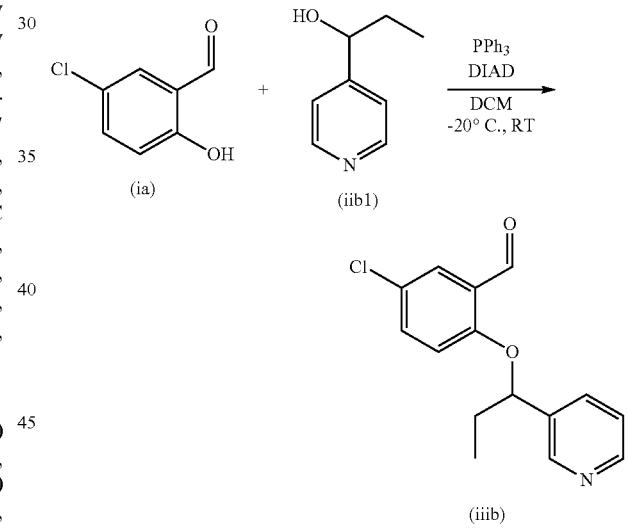

5-chlorosalycil aldehyde (intermediate (ia)) (200 mg, 1.27 mmol), 1-(pyridin-4-yl)propan-1-ol (intermediate (iib1) obtained above) (350 mg, 2.54 mmol) and PPh$_3$ (732 mg, 2.8 mmol) were dissolved in 20 ml of dichloromethane and cooled to −20° C. with an ice-salt bath. A solution of DIAD (550 μL, 2.8 mmol) in 5 mL of dichloromethane was added dropwise. Upon addition the reaction was warmed up to room temperature and continued for 3 hours. Solvent was evaporated and residue absorbed on silica gel. Flash chromatography purification gave 175 mg of product (iiib) as a yellow solid. Yield: 50%. $^1$H NMR (400 MHz, Chloroform-d) δ: 10.49 (s, 1H), 8.71 (d, J=6.2 Hz, 2H), 7.80 (d, J=2.8 Hz, 1H), 7.55 (d, J=9 Hz, 1H), 7.42 (d, J=6.2 Hz, 2H), 4.63 (t, J=6.4 Hz, 1H), 1.77 (qd, J=7.4, 6.4 Hz, 2H), 1.03 (t, J=7.4 Hz, 3H). $^{13}$C NMR (400 MHz, Chloroform-d) δ: 188.62, 159.61, 149.97, 145.74, 134.24, 130.51, 126.80, 125.00, 120.58, 114.62, 75.97, 32.51, 9.82.

Step 3—Formation of Intermediate (vc)

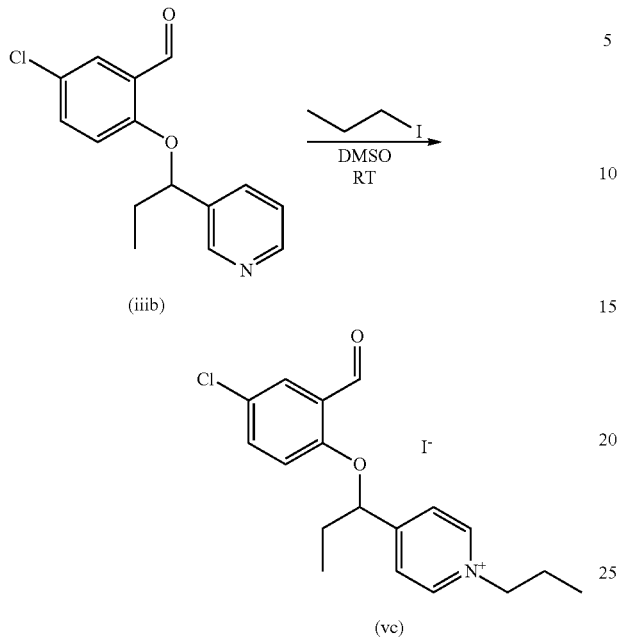

Alkylation of intermediate (iiib) was performed as shown for intermediate (va) to lead to intermediate (vc). Yield: 92%. $^1$H NMR (400 MHz, DMSO-d$_6$) δ: 10.45 (s, 1H), 9.08 (d, J=6.8 Hz, 2H), 8.03 (d, J=6.4 Hz, 2H), 7.84 (d, J=2.4 Hz, 1H), 7.56 (dd, J=8.8, 2.4 Hz, 1H), 7.21 (d, J=8.7 Hz, 1H), 5.74 (s, 2H), 4.70 (t, J=7.4 Hz, 2H), 4.59 (t, J=6.2 Hz, 1H), 2.03-1.98 (m, 2H), 0.96 (t, J=7.4 Hz, 3H), 0.88 (t, J=7.4 Hz, 3H). 13C NMR (101 MHz, DMSO) δ: 189.25, 158.42, 156.24, 144.86, 136.54, 128.91, 125.57, 124.99, 121.52, 112.90, 75.40, 68.05, 61.79, 31.07, 23.57, 11.03.

Step 1—Formation of Intermediate (iic)

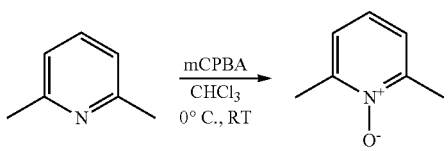

2,6-lutidine (2 mL, 17.3 mmol) was dissolved in 10 mL of chloroform and the solution was cooled down to 0° C. mCPBA (3 g, 17.4 mmol) was added portionwise to the stirred solution. The solution was kept for 1 h at 0° C. and slowly warmed up to room temperature and kept stirred for further 9 hours. Solid K$_2$CO$_3$ (2.4 g, 70 mmol) was added to the solution and stirred for additional 30 minutes. The solid was removed by filtration, the filtrate was dried over anhydrous sodium sulfate and concentrated under reduced pressure, to afford 1.7 g of 2,6-lutidine-N-oxide as a transparent oil. Yield: 80%. $^1$H NMR (400 MHz, Chloroform-d) δ: 7.21 (d, J=6.3 Hz, 2H), 7.08 (d, J=6.3 Hz, 1H), 2.45 (s, 6H). $^{13}$C NMR (101 MHz, Chloroform-d) δ: 156.21, 150.45, 118.04, 26.35.

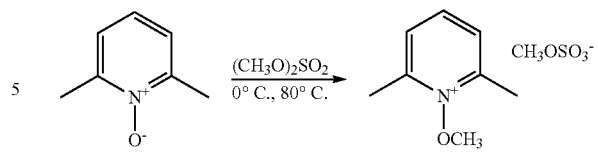

2,6-lutidine-N-oxide (1.5 g, 12.2 mmol) was introduced into a schlenk vessel under nitrogen atmosphere. The vessel was cooled to 0° C. and dimethylsulfate (1.15 mL, 12.2 mmol) introduced via syringe over 5 minutes. The reaction was then heated to 80° C. and stirred for 3 hours. The crude mixture was concentrated to dryness and the residue recrystallized from dry acetone to give 2.4 g of the product as colorless needles. Yield: 80%. $^1$H NMR (400 MHz, Chloroform-d) δ: 8.28 (d, J=7.9 Hz, 1H), 7.79 (d, J=7.6 Hz, 2H), 4.45 (s, 3H), 3.46 (s, 3H), 2.66 (s, 6H). 13C NMR (101 MHz, Chloroform-d) δ: 153.28, 148.56, 128.41, 69.65, 54.46,

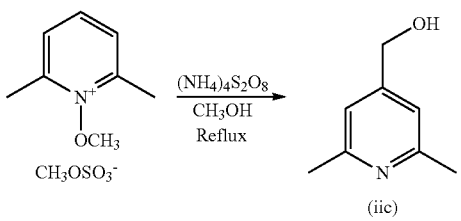

Lutidine-N-methoxide (2 g, 8 mmol) was dissolved in 25 mL of methanol and heated to reflux. To this mixture a solution of ammonium persulfate (456 mg, 4 mmol) in 3 mL of water was added. The reflux was continued for 1 hour. The crude was cooled to room temperature, and pH was adjusted to 7 using 10% NaOH. The crude was filtered and evaporated to dryness. The final compound was purified on silica gel, to obtain 440 mg of the desired intermediate (iic) as a white solid. Yield: 40%. 1H NMR (400 MHz, Chloroform-d) δ: 6.88 (s, 2H), 4.58 (s, 2H), 2.41 (s, 6H). 13C NMR (101 MHz, Chloroform-d) δ: 157.78, 150.71, 117.80, 63.43, 24.27.

Step 2—Formation of Intermediate (iiic)

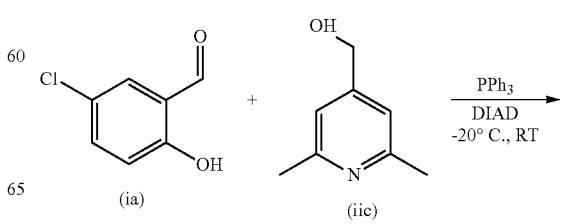

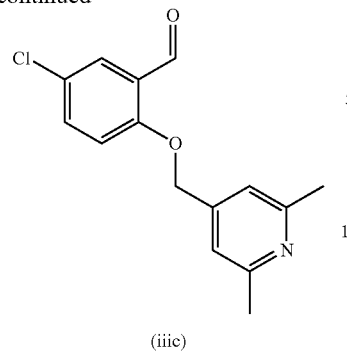

(iiic)

The intermediate (iiic) was prepared as described above, starting from 5-chlorosalycil aldehyde of Formula (ia) (200 mg, 1.27 mmol) and (2,6-dimethylpyridin-4-yl)methanol (350 mg, 2.54 mmol), intermediate (iic) obtained as described above. Yellow solid, 144 mg. Yield: 40%. $^1$H NMR (400 MHz, Chloroform-d) δ: 10.42 (s, 1H), 7.82 (d, J=2.9 Hz, 1H), 7.50 (dd, J=8.9, 2.9 Hz, 1H), 7.02 (d, J=8.9 Hz, 1H), 6.90 (s, 2H), 4.45 (s, 2H), 2.34 (s, 6H). $^{13}$C NMR (101 MHz, Chloroform-d) δ: 188.12, 156.80, 149.71, 145.67, 134.55, 127.83, 127.31, 126.35, 120.67, 118.30, 64.03, 24.83.

Step 3—Formation of Intermediate (vd)

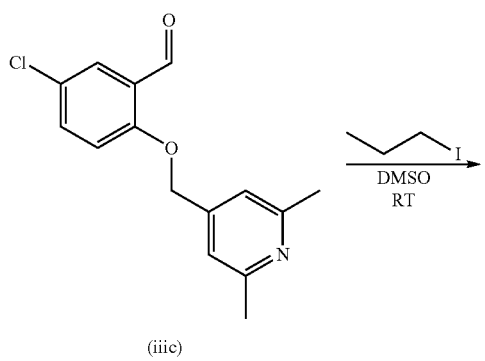

Alkylation of intermediate (iiic) obtained above was performed as shown for intermediate (va) to lead to intermediate (vd). Yield: quantitative. 1H NMR (400 MHz, DMSO-d$_6$) δ: 10.40 (s, 1H), 8.10 (s, 2H) 7.93 (d, J=2.7 Hz, 2H), 7.81 (d, J=2.4 Hz, 1H), 7.52 (dd, J=8.8, 2.4 Hz, 1H), 7.24 (d, J=8.7 Hz, 1H), 5.65 (s, 2H), 4.62 (t, J=7.4 Hz, 2H), 2.35 (s, 6H), 2.00 (t, J=7.3 Hz, 2H), 0.98 (t, J=7.4 Hz, 3H). $^{13}$C NMR (101 MHz, DMSO-d$_6$) δ: 189.42, 157.30, 149.51, 146.67, 134.35, 128.06, 127.42, 126.88, 120.15, 119.30, 67.54, 65.24, 26.02, 25.33, 12.11.

Step 1—Formation of Intermediate (iiid)

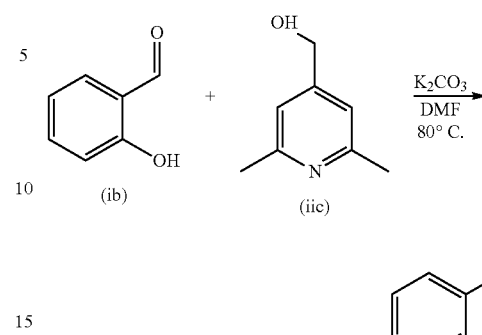

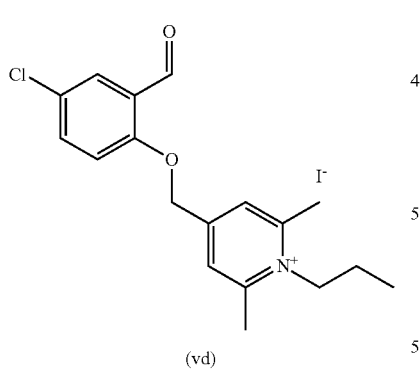

Synthesis of intermediate (iiid) was performed as for compound (iiia), starting from 435 μL (4.1 mmol) of salycilaldehyde ((ib)), 1.5 g of pyridine derivative (iic) (6.15 mmol) and 1.7 g of K$_2$CO$_3$ (12.3 mmol) in 40 mL of DMF. Yield: 55%. 1H NMR (400 MHz, Chloroform-d) δ: 10.61 (s, 1H), 8.68 (d, J=6.0 Hz, 2H), 7.91 (dd, J=7.7, 1.8 Hz, 1H), 7.56 (ddd, J=8.5, 7.3, 1.8 Hz, 1H), 7.40 (d, J=6.1 Hz, 2H), 7.11 (td, J=7.5, 0.9 Hz, 1H), 7.00 (td, J=8.4, 0.8 Hz, 1H), 5.25 (s, 2H). $^{13}$C NMR (101 MHz, CDCl$_3$) δ: 189.22, 160.22, 150.24, 145.13, 135.93, 129.09, 125.24, 121.58, 121.27, 112.71, 68.58.

Step 2—Formation of Intermediate (ve)

Alkylation of intermediate (iiid) (300 mg) obtained above was performed as shown for intermediate (va) to lead to intermediate (ve) as yellow to brown solid. Yield: 90%.

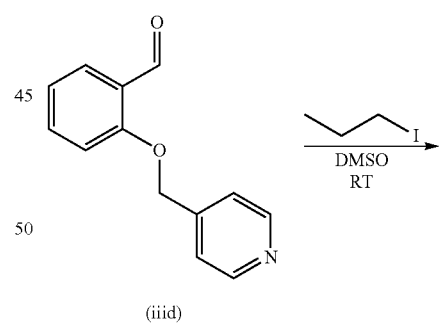

$^1$H NMR (400 MHz, DMSO-d$_6$) δ: 10.57 (s, 1H), 9.11 (d, J=6.8 Hz, 2H), 8.31 (d, J=6.7 Hz, 2H), 7.83 (dd, J=7.7, 1.8 Hz, 1H), 7.73 (ddd, J=8.5, 7.3, 1.9 Hz, 1H), 7.31 (dd, J=8.5, 1.0 Hz, 1H), 7.27-7.15 (m, 1H), 5.69 (s, 2H), 4.61 (t, J=7.4 Hz, 2H), 2.03-1.91 (m, 2H), 0.92 (t, J=7.4 Hz, 3H). $^{13}$C NMR (101 MHz, DMSO) δ: 190.01, 159.71, 156.72, 145.06, 136.87, 129.31, 125.57, 125.09, 122.22, 114.22, 67.95, 62.19, 24.57, 10.71.

Further pro-fluorophores of the invention of Formula (I) were obtained as for compound (1) from the corresponding aldehyde intermediates (vc), (vd), (ve) and reacting those with a

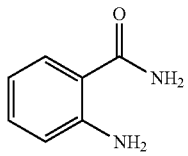

diamine of formula (via) as defined above or (ib) to lead to pro-fluorophores (5), (6) and (7), respectively which were tested and behaved similarly to compounds (1) to (4).

(5)

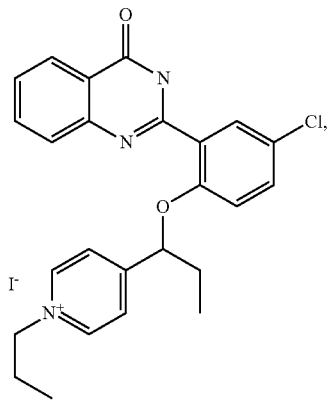

(6)

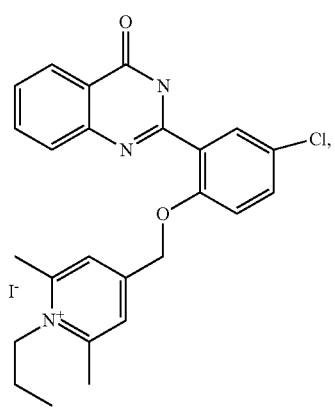

(7)

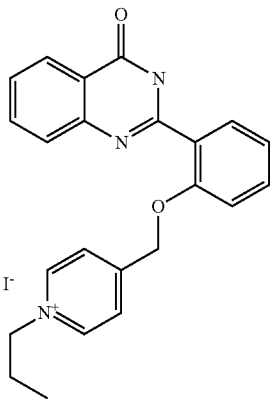

Synthesis of the compound (6) was performed from 111 mg of aldehyde (0.29 mmol) leading to a white solid. Yield: 60% $^1$H NMR (400 MHz, DMSO-d$_6$) δ: 9.07 (d, J=6.8 Hz, 2H), 8.21 (d, J=6.4 Hz, 2H), 8.14 (s, 1H), 7.64 (dd, J=7.7, 1.6 Hz, 1H), 7.53 (dd, J=7.5, 1.7 Hz, 1H), 7.36 (ddd, J=8.8, 7.4, 1.7 Hz, 1H), 7.26 (ddd, J=8.2, 7.2, 1.7 Hz, 1H), 7.11-7.02 (m, 2H), 6.78 (dd, J=8.2, 1.0 Hz, 1H), 6.70 (ddd, J=8.0, 7.2, 1.1 Hz, 1H), 6.26 (s, 1H), 5.54 (s, 1H), 4.56 (t, J=7.3 Hz, 2H), 2.01-1.88 (m, 2H), 0.90 (t, J=7.4 Hz, 3H). 13C NMR (101 MHz, DMSO-d$_6$): δ 164.24, 157.40, 155.01, 148.55, 146.32, 144.93, 138.00, 133.80, 130.25, 129.79, 128.49, 125.96, 121.81, 117.61, 115.18, 114.91, 112.91, 67.78, 62.16, 24.54, 10.72.

Example 2: Preparation of Probes for the Target Molecules for Use in a Method According to the Invention In a method according to the invention the detection of a target molecule in a sample is achieved though the detection of the formation of an insoluble fluorophore once a corresponding profluorophore is in the vicinity of a photoredox catalyst bound to a target molecule in a sample, thereby enabling the detection and quantification of said target molecule.

Probes

In order to achieve the photoredox catalyst to be bound to the target molecule, the probes labelled with the said photoredox catalyst needs to have a specific affinity for the target molecule.

In order to get the target molecule bound to the anchoring substrate where the photoreaction may occur, the anchoring substrate should have a specific affinity for the target molecule (e.g. substrate comprising a probe having specific affinity for the target molecule) or to a label bound to the target molecule (streptavidin group that can react with a biotin group conjugated to a probe having specific affinity for the target molecule).

In order to get the pro-fluorophore more efficiently in the vicinity of a target molecule, a pro-fluorophore of the invention can be also conjugated to a moiety having a specific affinity for the target molecule and be used as "Velcro" nucleic acid sequence as described in Example 7. In this case, according to a particular embodiment, the photoredox catalyst labelled probe and the pro-fluorophore labelled probe recognize portion of the target sequences which are located in the vicinity on the sequence of the target molecule.

Those moieties can therefore be, for example, nucleic acid probes such as DNA, RNA, a peptide nucleic acid (PNA), locked nucleic acids (LNA) or any mixture of DNA, RNA, PNA, LNA not limited to the four natural bases A, T, C and G which specifically recognize at least a portion of the target molecule sequence.

The DNA probes can be any known short sequences that have a specific affinity for the target molecule. In the field of food, in particular, meat, it may be difficult to find short DNA probes specific for one meat in order to detect potential contaminants from another type of meat. As an illustrative example of identification of specific short DNA probes in this field, the mitochondrial gene COI (cytochrome c oxidase) was chosen since it is used as the standard DNA barcode for animals due to its rapid evolution. At the same time, mitochondria are present in high number (200-1000 copies/cells) therefore increasing the abundance of the target DNA compared to genomic background. The mitochondrial DNA of 15 animals, including 12 generally used for meat production (Chicken, Guinea-fowl, Donkey, Horse, Lamb, Dromedarius, Camel, Beef, Pork, Turkey, Monkey and Goat) together with potential lab contaminants (Human, Mouse, Rat) was downloaded from the NCBI (National Center for Biotechnology Information) database and the barcode region identified as described in Ivanova et al., 2012, *Methods Mol. Biol.*, 858: 153-82). By aligning sequences, one 74 bp pork DNA region with most divergence could be identified as specifically present in one organism (FIG. 2) and the DNA probes specific for pork could be designed on this basis.

PNA probes compared to DNA have the following advantages: i) to weakly bind to RNA or DNA molecules that have one single mismatch, thus increasing selectivity; ii) to bind to target RNA/DNA molecules independently of the concentration of salts in the medium, so the salts concentration in the reaction can be minimized to increase selectivity; iii) to be resistant to cellular degrading enzymes, allowing to use less probe and thus minimize off-target hybridizations. LNA as compared to PNAs have the following advantages: i) LNA-DNA chimeras can be easily synthesized in the lab as it is based on phosphoramidite chemistry, this allow increasing the melting temperature of the probe while minimizing the number of nucleotides. A minimal number of nucleotides is important to discriminate single-nucleotide polymorphisms; ii) higher aqueous solubility compared to PNA.

DNA Probes can be synthetized at low-cost and potentially printed on a support such as paper and used according to standard lateral flow technologies previously developed for antibody-based assays (i.e. pregnancy test).

Methods of Coupling

The coupling of the probe, in particular the nucleic acid probes, to the photoredox catalyst can be prepared by methods described in Sadhu et al., 2013, supra or as described below.

Further, the coupling of the probe, in particular the nucleic acid probes to a pro-fluorophore of the invention can be prepared by methods described in Sadhu et al., 2013, supra or as described below.

For example, a probe according for use in a method according to the invention can comprise a linker between two nucleic acid sequences such as a PNA and another PNA, such as a polyethylene glycol (PEG) moiety for improving probe flexibility and water solubility.

According to a particular aspect, pro-fluorophore conjugates of Formula (II) could be prepared by coupling a pro-fluorophore of Formula (I) with a spacing moiety (a) and (b) a docking moiety as defined herein through standard coupling reactions leading to 4 mer γD-PNA pro-fluorophore conjugates of Formula (IIa) or (IIb) as shown below. Automated synthesis was performed as previously reported in Sadhu et al., 2013, *Chemistry—a European Journal*, 19, 8182-8189 wherein profluorophore (2) was coupled on the resin via [3+2]cycloaddition. Compound (2) was dissolved in 50 μL of NMP to obtain a 0.1 M solution. 2 mg of TBTA was added as solid. 15 μL of a 0.4 M solution of $CuSO_4$ in water was added, followed by 50 μL of 2 M aqueous solution of ascorbic acid. The yellow solution was transferred on the resin and reacted overnight. Final compounds were purified by reverse-phase HPLC. The PNA-profluorophore of Formula (IIa) (conjugate of Formula (II) wherein R13a is a linking group of Formula (III) wherein m is 0 and $R_{11c}$, $R_{12b}$, $R_{14g}$ and $R_{15d}$ are absent) has a calculated MW ($C_{78}H_{91}Cl_2N_{32}O_{19}^+$): 1851.69 Da. LCMS m/z found: 1234.58 $[2M+H]^{3+}$, 926.42 $[M+H]^{2+}$, 618.08 $[M+2H]^{3+}$. MALDI-TOF m/z found: 1545.563 $[M-QPD]^+$.

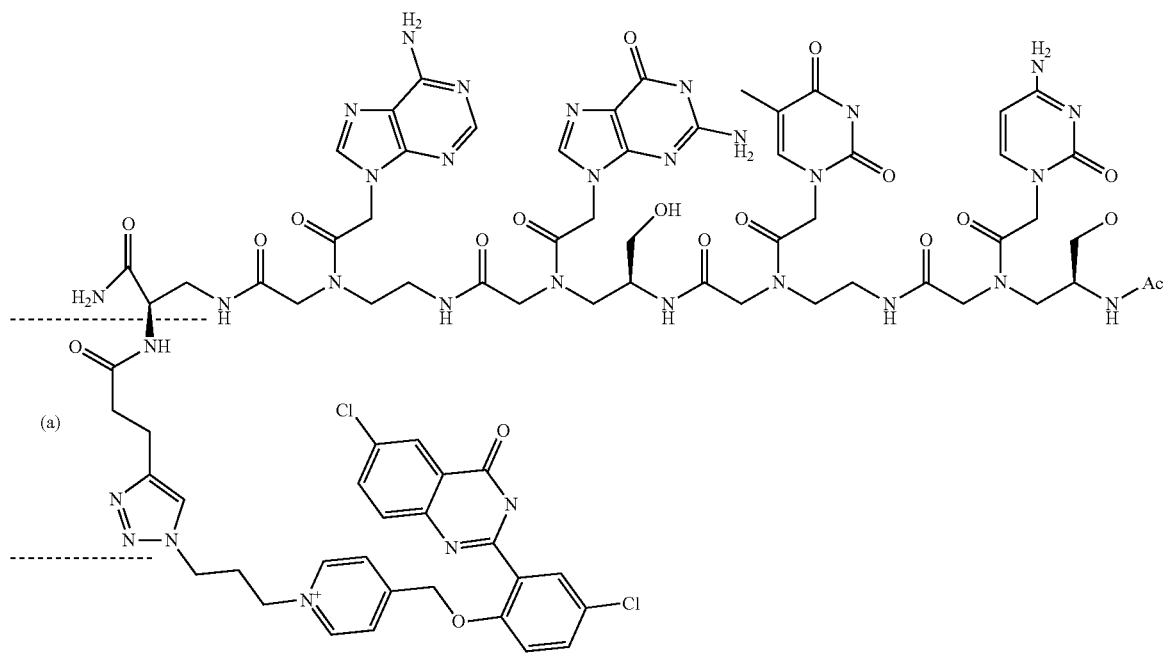
(IIa)
The PNA-PEG-profluorophore of Formula (IIb) (conjugate of Formula (II) wherein R13a is a linking group of Formula (III) wherein m is 1, n is 2 and $R_{11c}$, $R_{12b}$, $R_{14g}$ and $R_{15d}$ are absent) has a calculated MW ($C_{84}H_{102}Cl_2N_{33}O_{22}^+$): 1996.85 Da. LCMS m/z found: 1330.83 [2M+H]$^{3+}$, 999.08 [M+H]$^{2+}$, 666.42 [M+2H]3+. MALDI-TOF m/z found: 1690.226 [M-QPD]$^+$.

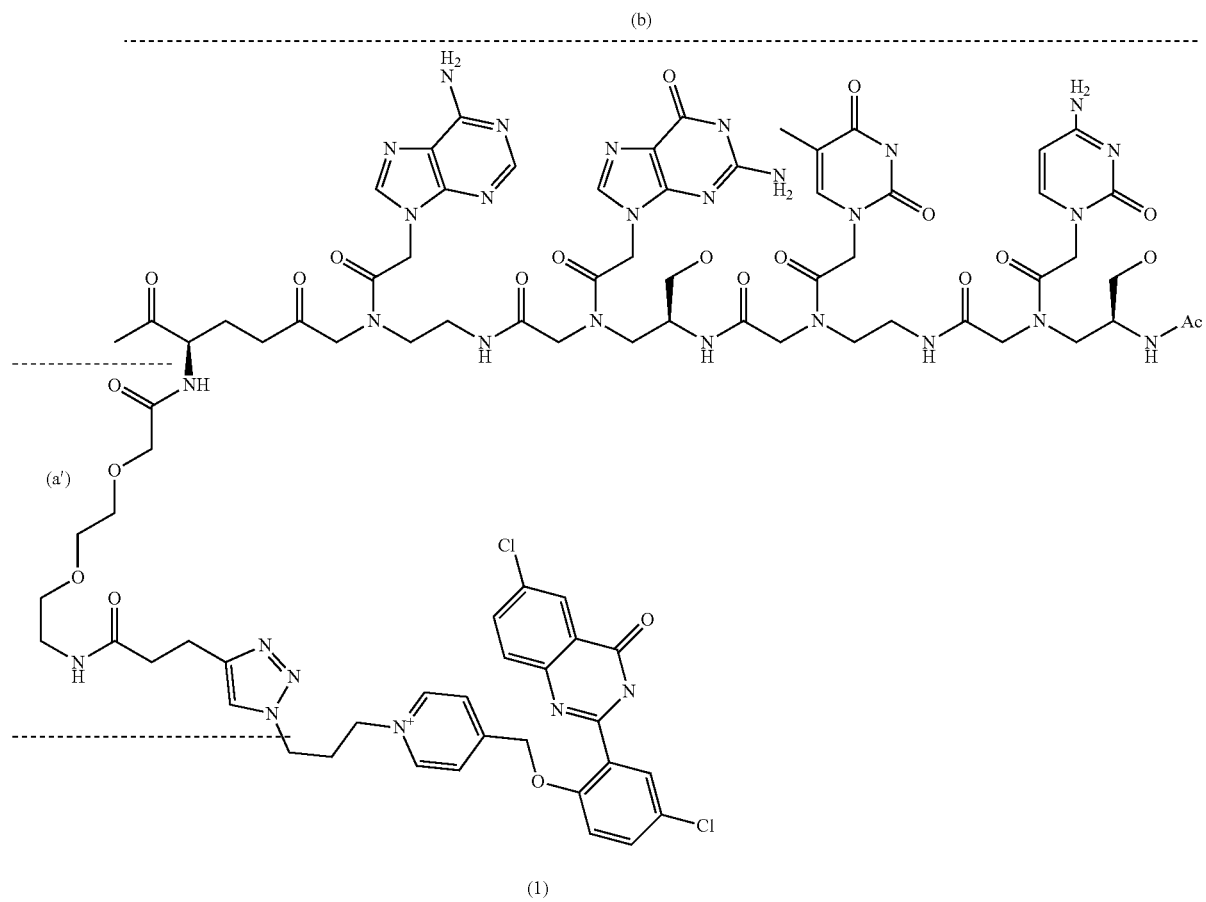

The compounds were tested and shown to be functional in templated reactions such as described in the context of the present invention.

Example 3: An Assay for Detection of a Target DNA in a Sample with a Pro-Fluorophore of the Invention on a Test Strip A general principle of a method of detection of the invention for detecting a DNA target molecules in a sample by photochemical reaction was tested as depicted under FIG. 1.

Compound (1) was dissolved in pure water and diluted to 2 mM. An anchoring probe (Biotinylated PNA that recognizes the target molecule (FIG. 1A*a*) and a catalytic probe (Ru-PNA that recognizes the target molecule conjugated to the transition metal complex photoredox catalyst, $Ru(bpy)_3Cl_2$ (FIG. 1A*b*) were used at 10 nM concentration. The PNA probes were dissolved in PBS 1× to obtain a 200 nM solution. Sodium ascorbate ((NaAsc, reducing agent) was dissolved in water to obtain a 30 mM solution. The PNA probes and the reducing agent were mixed in equal volumes, 30 μL each, to obtain a 90 μL working solution.

Step (i):
A sample (FIG. 1A*c*) containing various concentrations (50 nM, 100 nM, 250 nM, 500 nM, 1000 nM in 60 μl phosphate buffered saline pH 7.4) of a target DNA molecule comprising regions complementary to each of the PNA probes is contacted with the mixture containing the PNA probes and the reducing agent prepared as described above for the probes to bind the target DNA such that hybridization results in a complex where the target DNA molecule is labelled with both biotin and ruthenium. Further, the sample is contacted with an anchoring substrate (FIG. 1A*d*) in the form of a lateral flow dipstick containing immobilized streptavidin such that during the flow of the liquid solution on the test strip, the formed complex is captured onto the surface of the dipstick through streptavidin-biotin interaction (FIG. 1A*f*).

Step (ii)
The dipstick is contacted with a pro-fluorophore of the invention present in the sample solution and irradiated for 5 minutes using a 455 nm LED lamp to promote the photochemical reaction between the pro-fluorophore at the position of the photoredox catalyst bound to the dipstick surface, resulting in the chemical bond cleavage (FIG. 1A*g*) leading to the formation of the corresponding fluorophore which precipitates on the dipstick and forms a green fluorescent band (FIG. 1A*h*).

Step (iii)
The green fluorescent fluorophore can be visualized on the anchoring dipstick under a black light (365 nm UV lamp) and the concentration of the target DNA can be derived therefrom. A negative control is run in absence of the photocatalyst-labelled PNA probe (FIG. 1B).

Example 4: An Assay for Detection of a DNA of Porcine Origin

The method of the invention was tested for its ability to detect a target DNA sequence from pork origin in a sample with the use of DNA probes specific for two porcine DNA fragments.

Probe Molecules

Two "Velcro" probes comprising two different nucleic acid sequences which are specific for pork DNA specific region as identified under Example 2 (CAGCCCG-GAACCCTACTTGGCGATGATCAAATCTATAATG, SEQ ID NO: 3). Probe 1 (referred to as L') was used as an anchor capture immobilized on a anchoring substrate in the form of streptavidin-agarose beads and comprises a nucleic acid sequence of SEQ ID NO: 1 (CTTGGGATGAAC) that hybridizes to a part of target DNA sequence (part L). Probe 2 (referred to as R') was used as catalyst probe comprising a nucleic acid of SEQ ID NO: 2 (CTACTAGTTTAGAT) that hybridizes to a part of target DNA (part R) and was conjugated to a catalyst (Ru(bpy)$_2$Phen) as described in Example 2.

Titration of streptavidin-agarose beads loaded with stoichiometric (1:1:1) concentrations (50 nM, 100 nM, 250 nM, 500 nM, 1000 nM in 60 µl phosphate buffered saline pH 7.4) of a target pork mitochondrial DNA, Probe 1, Probe 2 and ascorbic acid (reducing agent) were tested in a method according to the invention using a pro-fluorophore according to the invention (compound 1).

In a first step, the sample solution, the anchoring substrate (beads) comprising the anchoring probe and the catalyst probe were mixed together allowing the DNA probes (L' and R') to bind to a respective L and R portion of the target DNA (FIG. 2A) leading to the target molecule being anchored onto the bead's surface through immobilized probe-DNA conjugates as shown on FIG. 2. The beads are then washed with phosphate-buffered saline (PBS) and the beads are re-suspended in 50 µl PBS containing 100 µM of a pro-fluorophore of the invention and 100 mM ascorbic acid (reducing agent). The pro-fluorophore was reduced in presence of the catalyst conjugated to probe R' within 10 minutes resulting in a fluorescence signal in the solution (FIG. 2B). The limit of fluorescent signal detection with naked eye was found to be reached for a sample comprising 100 nM mitochondrial DNA that corresponds to 0.1 mg of pork meat.

In conclusion, an assay based on a method according to the invention is an efficient tool for the rapid detection (within about 10 min) of the presence of pork DNA fragments in a sample through a fluorescence signal without a need to use laboratory instruments, toxic reagents or complex bioinformatics analysis.

Example 5: Increased Selectivity for DNA Detection of Porcine Origin

A probe must be specific, selective and sensitive for a target DNA molecule in order to be used in for detection of this DNA in a sample. On anchor probes and catalytic probes typically only 2 or 3 nucleotides are specific. Therefore, given these small differences no hybridization technique developed so far could be selective, which means that although a probe may be specific for pork's DNA, it may also bind cow's DNA, resulting in a false positive result of used assay.

To improve selectivity of the assay described in Example 4, chemical PNA probes were used, which are designed to be complementary to the pork DNA mini-barcode of FIG. 3 due to Watson/Crick nucleobase pairings. The probe selectivity was further increased by use of short sequences (as described in example 4) as these are more resistant to mismatches than longer probes. Therefore, an assay was designed with three short PNA probes prepared as described above, instead of one long probe, wherein a target DNA of porcine origin can be detected only if the three PNA-probes are hybridized on the same DNA molecule as shown on FIG. 4. A first anchoring probe (CGCGACTTGATCCAG, SEQ ID NO: 6) specific for pork's DNA is used to immobilize the target pork DNA on a test strip and resulting on an anchoring substrate having a fixed pork target DNA referred to as anchored target DNA (FIG. 4A). A second and a third DNA probes are used for contacting the anchored target DNA, wherein the second probe (CTTGGGATGAAC, SEQ ID NO: 1) is a "catalyst probe" comprising a PNA nucleic acid sequence that recognizes specifically a region of the anchored pork target DNA due to nucleobase pairings and a transition metal complex photoredox catalyst (Cat.) and the third probe (CTACTAGTTTAGAT, SEQ ID NO: 2) comprises a PNA nucleic acid sequence that recognizes specifically a region of the anchored pork target DNA due to nucleobase pairings (different from the region recognized by the second probe) conjugated to a profluorophore of the invention (Pro-Fl.) (FIG. 4B). When the catalyst probe and the probe bearing the profluorophore hybridize on the anchored target DNA molecule under the suitable conditions for photocatalysis (reductive medium and light excitation), due to the small size of the target DNA molecule, the catalyst and the profluorophore are maintained in a sufficient vicinity to initiate the photocatalysis of the pro-fluorophore and the release of the fluorophore (Fl.) (FIG. 4C) which can be then detected by a naked eye.

The use of the above probes allowed to report at least 1% w/w pork meat in a beef based product, after 20 minutes. This is the threshold that regulatory agencies usually consider as positive for contamination/mislabelling.

Example 6: Detection of a Target DNA and Multiplexing

Further examples of possible constructs used in a method of the invention are provided below.

a) Detection of a Target DNA after DNA Amplification

There may be instances in which the concentration of target nucleic acid is below the sensitivity of the method. This could be the case for food safety (i.e. for the detection of undesired bacteria like *Salmonella, Campylobacter, Lysteria*) or in the frame of Halal/Kosher certification in which traces of pork DNA are undesired. When the method requires high sensitivity, it is possible to increase the concentration of target nucleic acids by specific synthesis. In the first step, target dsDNA (i.e. pork) is amplified with primers (F1 and R1) specific for different regions of this target DNA (F1' and R1'). One primer (F1) is an anchoring probe comprising a DNA probe specific to region F1' of the target DNA, conjugated with biotin and the second primer (R1) is a catalyst probe comprising a DNA probe specific to region R1' of the target DNA, conjugated with a photoredox catalyst (Ru bpy$_2$ Phen). Amplification is performed by polymerase chain reaction (PCR) or any of the known isothermal reactions. If the target nucleic acid is RNA-based (i.e. Hepatitis A virus), a polymerase with reverse transcription activity may be preferred. At the end of the amplification, a DNA sequence is obtained that contains biotin at one end and the catalyst at the other end (FIG. 5A).

A lateral flow strip device with a detection line made of immobilized streptavidin and a bottom pouch containing a mixture of a profluorophore (pro-dye) according to the invention and a reducing agent (ascorbic acid) (FIG. 5B) is used as anchoring substrate.

The test strip is immersed in the vessel containing DNA amplification medium containing the resulting the target DNA sequence labelled with both biotin and the catalyst, the pro-dye and the ascorbic acid to moving by capillarity along the strip (FIG. 5C). The amplified target DNA is then captured on the detection line (anchoring substrate) through streptavidin-biotin interaction. Next, the catalyst on the target DNA sequence transforms the pro-dye into the corresponding dye which precipitates on the detection line (FIG. 5D) and can be detected. The color change on the detection line is the indicative of the presence of the target DNA in the sample.

b) Detection of a Target DNA by Strand-Invasion

In Example 6a, the detection of target DNA with a method according to the invention is dependent on the choice of primers used for the amplification of target DNA. This constraint can be circumvented adopting a strand-invasion strategy. Two probes are designed comprising a nucleic acid sequence (e.g. PNAs) complementary to two specific regions F1' and R1' of the target dsDNA. The first probe has a nucleic acid sequence F1 complementary to target DNA sequence F1' and is conjugated to a nucleic acid sequence C1 which is complementary to an anchoring probe C1'. The second probe has a nucleic acid sequence R1 complementary to target DNA sequence R1' and is conjugated to a nucleic acid sequence R0 that is complementary to a probe R0' conjugated with a catalyst (catalyst probe) (FIG. 6A).

A lateral flow strip device with a detection line made of a anchoring probe C1' (i.e. PNA) complementary to the tail C1 of the first probe and a bottom pouch containing a mixture of a profluorophore (pro-dye) according to the invention, a reducing agent (ascorbic acid) and a detection probe R0' complementary to the tail R0 that is conjugated with a catalyst (FIG. 6B) is used as anchoring substrate. The probes F1-C1 and R1-R0 are incubated in a reaction tube with target DNA (#1) in appropriate buffer (i.e. PBS). The probes strand-invade the double strand target DNA creating a hybrid structure (FIG. 6A). The test strip is immersed in the reaction tube causing strand-invaded DNA complexes to be immobilized at the detection line, and a detection probe R0', a pro-dye and ascorbic acids to move upwards the stripe by capillarity (FIG. 6C). DNA complexes are captured on the detection line due to the C1' and C1 nucleic acids' hybridization and the catalyst transforms the pro-dye into the corresponding dye which precipitates on the detection line (FIG. 6D). The color change at the detection line is indicative of the presence of a target DNA in the sample (FIG. 6E).

c) Detection of a Mixture of Target DNAs by Strand-Invasion

Figure 7:
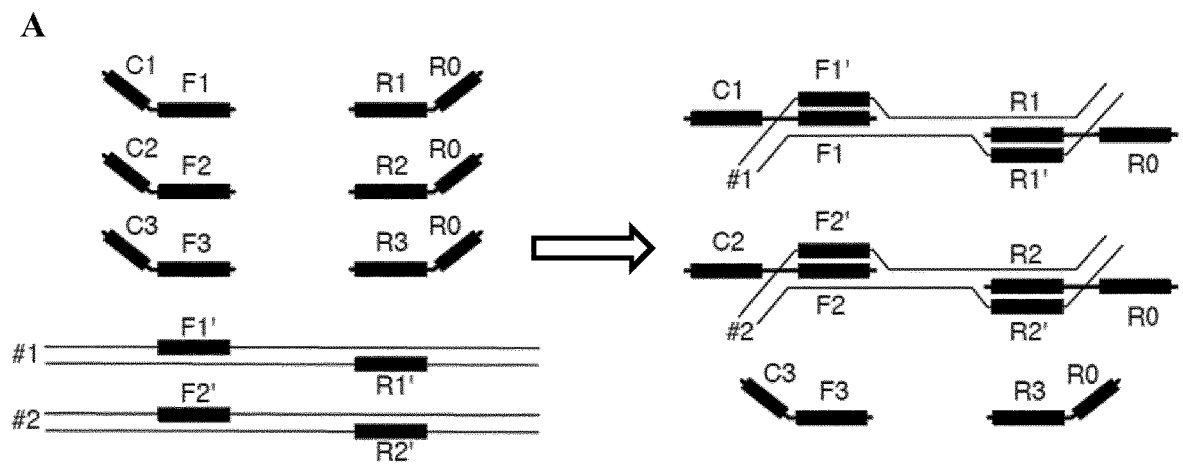
FIG. 7 schematically represents steps (A-D) of an assay for detection of multiple DNA fragments in a sample by strand-invasion and DNA-templated reaction as described in Example 6.
Figure 7:
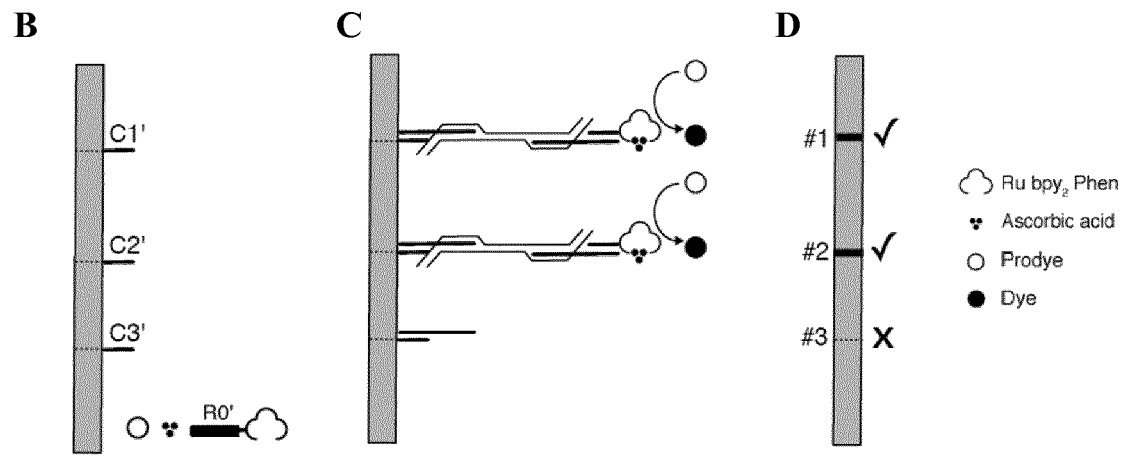
Figure 8:
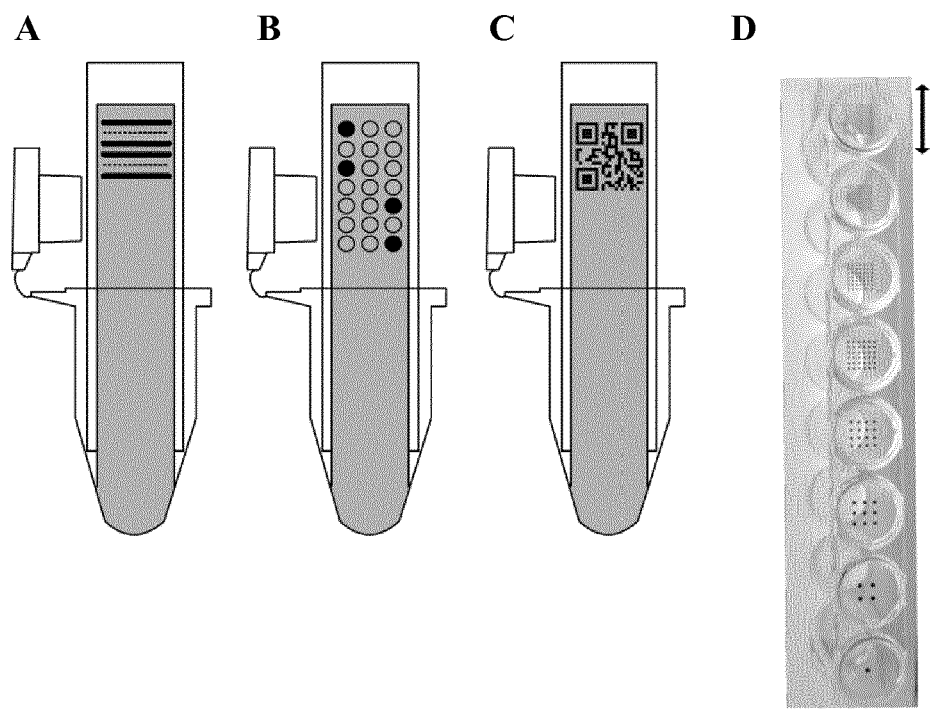
FIG. 8 schematically represents read outs of test results as described in Example 6. A: barcode; B: macro array code; C: QR™ code; D: array spotter (arrow scale bar—5 mm).

Mixtures of target DNAs can be also detected in a method according to the invention as exemplified in FIG. 7.

Several probes comprising a nucleic acid sequence (e.g. PNAs) complementary to several target DNA sequences are designed. For each target dsDNA, two probes comprising a nucleic acid sequence complementary to two different specific target DNA regions are designed. For example, for target dsDNA #1 probes are complementary to regions F1' and R1' respectively, for target dsDNA #2 probes are complementary to regions F2' and R2', for target dsDNA #3 probes are complementary to regions F3' and R3'. The first probe from a pair has a nucleic acid sequence (e.g. F1, F2, F3) complementary to target DNA sequences (e.g. F1', F2', F3') and is conjugated to a nucleic acid sequence (e.g. C1, C2, C3) complementary to a capture probe (C1', C2', C3'). The second probe from each pair has a nucleic acid sequence (e.g. R1, R2, R3) complementary to target DNA sequences (e.g. R1', R2', R3') and is conjugated to a nucleic acid sequence R0 that is complementary to a probe R0' conjugated with a catalyst (FIG. 7A). A lateral flow device comprising an immobilized detection line made of a capture probe (C1', C2', C3') (i.e. PNA) complementary to the tail probe nucleotides (C1, C2, or C3 and a bottom pouch containing a mixture of a profluorophore (pro-dye) according to the invention, a reducing agent (e.g. ascorbic acid) and a detection probe R0' complementary to the tail R0 that is conjugated with a catalyst (FIG. 7B). The multiple probes pairs (F1-C1 and R1-R0, F2-C2 and R2-R0, F3-C3 and R3-R0) are incubated in a reaction tube with target DNAs (#1 and #2) in PBS. The probes strand-invade the double strand target DNA creating a hybrid structure (FIG. 7A). The test strip (FIG. 7B) is immersed in the reaction tube causing strand-invaded DNA complexes be immobilized at a detection line, and a detection probe R0', a pro-dye and ascorbic acids to move upwards the stripe by capillarity (FIG. 7C). DNA complexes are captured on the detection line due to the C1'/C2' and C1/C2 nucleic acids hybridization (FIG. 7C) and the catalyst transforms the prodye into the corresponding dye, which precipitates on the detection line (FIG. 7D). The color change at the detection line is indicative of the presence of target DNA in the sample (FIG. 7D).

Several types of readouts for the formation of the fluorophore in a method according to the invention applied to the detection of a multiple target DNAs may be used. For example, those include:

1) a barcode configuration (FIG. 8A) wherein capture probes for respective test DNAs are immobilized in a form of separate lines on a test strip;
2) a macro array code configuration (FIG. 8B) wherein capture probes for respective test DNAs are immobilized in a form of separate circles on a test strip;
3) QR™ code (Quick Response Code that is a type of matrix barcode or two-dimensional barcode) (FIG. 8C), wherein capture probes for respective test DNAs are immobilized in a form of matrix barcode on the test strip. The format of a QR™ code is of interest as it allows encrypting results of genetic test in a secure format that is not decodable without a key and thus can increase data security and privacy. This can also prevent from fraud of the test results;
4) an array spotter configuration (FIG. 8D) wherein assay compounds are placed as drops (e.g. 1-144 drops) within assay area (e.g. circles 5 mm in diameter, which is compatible with the constraints of a lateral flow strips and maintain optical resolution sufficient for the detection with naked eye or a smartphone camera). The array spotters can be manufactured with commercially available tools e.g. Scienion.

Example 7: Detection of a Target DNA in a Nucleic Acid "Templated" Reaction

An example of a method of the invention comprising the use of different stereochemistries (L, D) of PNAs is provided below which allows a nucleic acid templated reaction to proceed quickly as shown on FIG. 9. The following probes were used:

An anchoring probe 1 which comprises:
a 14 mer γL-PNA oligomer complementary to a target DNA (double stranded DNA, dsDNA);
a PEG linker and;
7 mer γD-PNA complementary to a 7 mer γD-PNA immobilized on the anchoring substrate, prepared according to Example 2.
A catalyst probe 2 which comprises:
a 14 mer γL-PNA oligomer different from 14 mer γL-PNA of probe 1, but complementary to a target DNA;
a PEG linker and;
a 4 mer γD-PNA (complementary to the 4 mer γD-PNA of probe 3) conjugated to a photoredox catalyst, prepared according to Example 2. A conjugate of a profluorophore of the invention 3 which comprises
a 4 mer γD-PNA complementary to the 4 mer γD-PNA of probe 2 conjugated to a profluorophore according to the invention of Formula (I), prepared according to Example 2.

An anchoring substrate (test strip) comprising a 7 mer γD-PNA complementary to a 7 mer γD-PNA of probe 1 prepared according to Example 2.

The 14 mer γL-PNA sequences of probes 1 and 2 are designed to bind in pair to a unique dsDNA sequence. Simultaneous variations of the 14 mer γL-PNA sequences of probes 1 and 2 allow discriminating between different dsDNA. Variation of the 7 mer γD-PNA on probe 1 and complementary 7 mer γD-PNA from anchoring substrate allows a different positioning of probe-DNA complexes on the anchoring substrate. The 4 mer γD-PNA of probe 2 is kept constant regardless of any variation of the other sequences and can only interact with the complementary 4 mer γD-PNA of probe 3. Different dsDNA and PNA-based probes combination can be incubated together and then separated by their specific interaction with the immobilized PNA strand.

First, probe 1, probe 2 and target dsDNA are dissolved in PBS to obtain a 200 nM of respective compound solutions. The solutions comprising probes 1, 2 and dsDNA are mixed allowing hybridization between a target dsDNA and PNA probes 1 and 2 (FIG. 9A), leading to the target DNA being labelled with the anchoring probe 1 and the catalytic probe 2 (FIG. 9B).

Next, the anchoring substrate (FIG. 9C) is added to the solution comprising the probe-DNA conjugate obtained above which is captured onto the anchoring substrate surface at the location (e.g. lane) where the 7 mer γD-PNA complementary to a 7 mer γD-PNA of probe 1 are immobilized (FIG. 9D). The anchoring substrate is then washed with PBS (500 nM in PBS) to remove unbound probe-DNA complexes and contacted with the pro-fluorophore conjugate 4 (FIG. 9E) in presence of a reducing agent (NaAsc 10 mM solution in water) leading to the further conjugation of the pro-fluorophore conjugate on the target DNA in close proximity of the catalyst moiety of the catalytic probe 2 (FIG. 9F). The substrate is then illuminated (e.g. at about 455 nm with LED lamp) to promote the photocatalytic reduction of the pro-fluorophore and the resulting fluorophore to precipitate at the reaction site (FIG. 9G) and forming a fluorescent band where complexes are bound to the substrate via anchoring probe 1.

Example 8: A Kit for Performing an Assay According to a Method of the Invention for Detection of a Target DNA/RNA Kits for performing a method of the invention for the detection of a target nucleic acid sequence are illustrated below. There are kits for example either allow performing an assay for detection of a target nucleic acid sequence wherein reaction of amplification was performed before the test (Example 7) or allow performing an assay for detection of a target nucleic acid without a prior reaction of amplification and thus would comprise material needed for sample preparation (e.g. material lysate) and amplification (probes, test device).

For example, is provided a kit comprising:
in lyophilized form: a catalytic probe (probe labelled with a photoredox catalyst) and an anchoring probe (probe enabling the target molecule to be anchored to the anchoring substrate), both probes having a specific affinity for different regions of the target molecule, optionally with amplification agents such as DNA polymerases, optionally with reverse transcriptases (in case the target analyte is RNA) optionally with ancillary enzymes like helicases, nicking enzymes or single-strand DNA binding proteins to stabilize the DNA extension reaction);
optionally a rehydration medium;
optionally a reaction vessel for conducting an amplification reaction, preferably enabling maintaining the temperature of the amplification medium at the amplification temperature;
optionally a sampling device such as a sample cruncher to disrupt the sample and extract target molecules from said sample;
a reducing agent and a pro-fluorophore according to the invention for example placed in a pouch of a test strip which also comprises an anchoring substrate having an affinity for the anchoring probe.

Example 9: Further Examples of Fluorophores of Formula (I')

In order to check the behaviour of various fluorophores of Formula (I') as possible QPD within the context of the invention, the following compounds have been synthesized and tested.

Fluorophore (9) (of Formula (I') Wherein $R_1$-$R_8$ are H)

Compound (9) was synthesized starting from 70 mg of 2-aminobenzamideamide (0.51 mmol) (vib) and 55 µL of salicylaldehyde (viib) (0.51 mmol) to lead to a white to yellow solid final product as shown below.

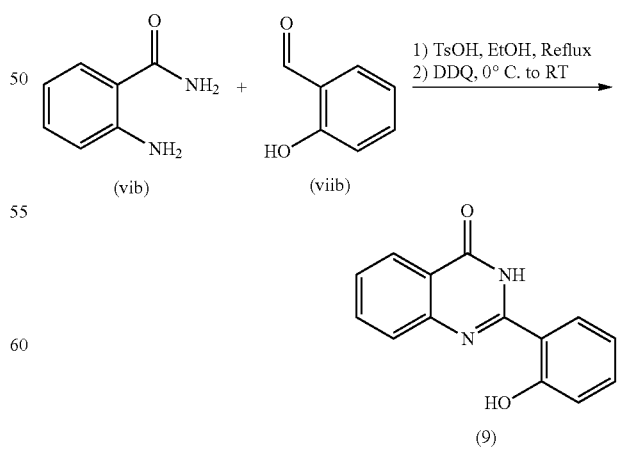

Yield: 65%. $^1$H NMR (400 MHz, DMSO-$d_6$) δ: 13.77 (s, 1H), 12.47 (s, 1H), 8.24 (dd, J=8.1, 1.6 Hz, 1H), 8.17 (dd, J=7.9, 1.5 Hz, 1H), 7.87 (ddd, J=8.5, 7.2, 1.6 Hz, 1H), 7.78 (dd, J=8.3, 1.1 Hz, 1H), 7.56 (ddd, J=8.2, 7.1, 1.2 Hz, 1H), 7.47 (ddd, J=8.6, 7.2, 1.6 Hz, 1H), 7.02 (dd, J=8.3, 1.2 Hz, 1H), 6.98 (ddd, J=8.2, 7.2, 1.2 Hz, 1H). $^{13}$C NMR (101 MHz, DMSO) δ: 161.84, 160.47, 154.17, 146.62, 135.51, 134.18, 128.18, 127.45, 126.54, 126.50, 121.22, 119.30, 118.34, 114.25.

Fluorophore (10) (of Formula (I') Wherein $R_1$, $R_3$-$R_5$, $R_7$-$R_8$ are H, $R_2$ is Cl and $R_6$ is —$CH_2$—C(O)—OMe)

Methyl 2-(4-hydroxyphenyl)acetate (3.31 g, 20 mmol), paraformaldehyde (3.3 g, 1:1 weight) and magnesium chloride (1.85 g, 20 mmol) were suspended in 75 ml of dry acetonitrile. Triethylamine (7 mL, 50 mmol) was added and the reaction refluxed for 3 hours. Upon completion, the acetonitrile was partially evaporated, the residue taken in diethyl ether and extracted with 1M HCl as shown below.

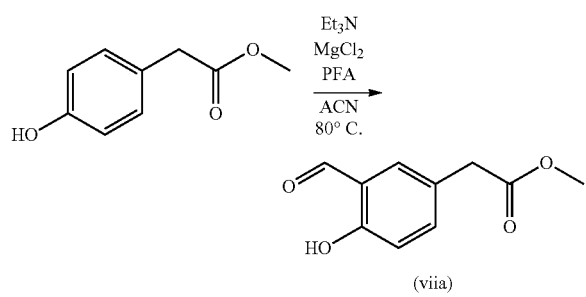

(viia)

The organic layer was dried over anhydrous sodium sulfate and the solvent evaporated under reduced pressure. The residue was purified by column chromatography to afford 2.3 g of the title compound as pinkish oil. Yield: 60%. $^1$H NMR (400 MHz, Chloroform-d) δ: 10.96 (s, 1H), 9.89 (s, 1H), 7.50 (d, J=2.3 Hz, 1H), 7.46 (dd, J=8.5, 2.3 Hz, 1H), 6.98 (d, J=8.5 Hz, 1H), 3.73 (s, 3H), 3.63 (s, 2H). 13C NMR (101 MHz, CDCl$_3$) δ 196.38, 171.70, 160.75, 138.03, 134.09, 125.48, 120.47, 117.93, 52.19, 39.79. Compound (9) was then synthesized in an open flask where methyl 2-(3-formyl-4-hydroxyphenyl)acetate obtained as described above (616 mg, 3.17 mmol), 2-amino-5-chloro benzamide (650 mg, 3.8 mmol) and TsOH.H$_2$O (300 mg, 1.58 mmol) were dissolved in 60 mL of methanol and refluxed for 6 hours as shown below:

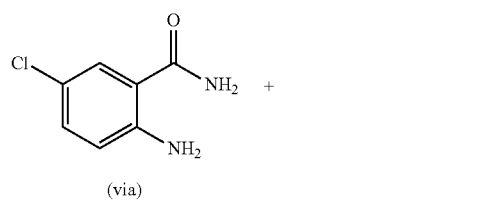

(via)

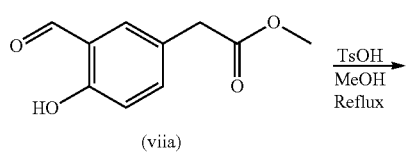

(viia)

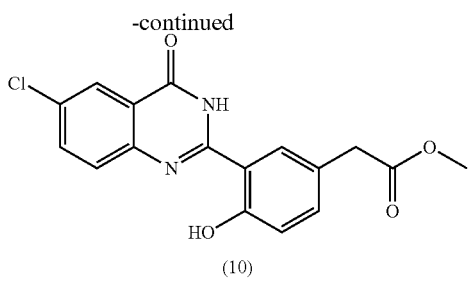

(10)

Compound (9) precipitated as the reaction proceeded and the yellow precipitate was isolated by centrifugation and washed three times with cold methanol. Yellow solid, 490 mg. Yield: 44%. $^1$H NMR (400 MHz, DMSO-d$_6$) δ: 13.12 (s, 1H), 12.50 (s, 1H), 8.12 (d, J=2.1 Hz, 1H), 8.09 (d, J=2.4 Hz, 1H), 7.89 (dd, J=8.7, 2.5 Hz, 1H), 7.83 (d, J=8.7 Hz, 1H), 7.37 (dd, J=8.4, 2.1 Hz, 1H), 6.99 (d, J=8.4 Hz, 1H), 3.66 (s, 2H), 3.64 (s, 3H). $^{13}$C NMR (101 MHz, DMSO-d$_6$) δ: 172.15, 160.84, 158.82, 154.14, 145.87, 135.43, 135.34, 131.52, 129.36, 129.04, 125.42, 122.52, 118.23, 114.44, 52.21.

Fluorophore (11) (of Formula (I') wherein $R_1$, $R_3$-$R_5$, $R_7$-$R_8$ are H, $R_2$ is Cl and $R_6$ is —$CH_2$—C(O)—OH)

Compound (11) was synthesized starting from methyl 2-(3-(6-chloro-4-oxo-3,4-dihydroquinazolin-2-yl)-4-hydroxyphenyl)acetate (compound (10) obtained as described above) (70 mg, 4.9 mmol) which was suspended in a 1:1 mixture of dioxane and 10% NaOH solution in water (10 mL total) and heated to 80° C., while stirring. Heating was maintained for 6 hours, until the parent compound was completely consumed. The solvent volume was reduced by evaporation and the residue purified by reverse phase chromatography to give a yellow solution. pH of the solution was adjusted to 5 with HCl and the residue filtered and washed with cold water then cold acetone as shown below:

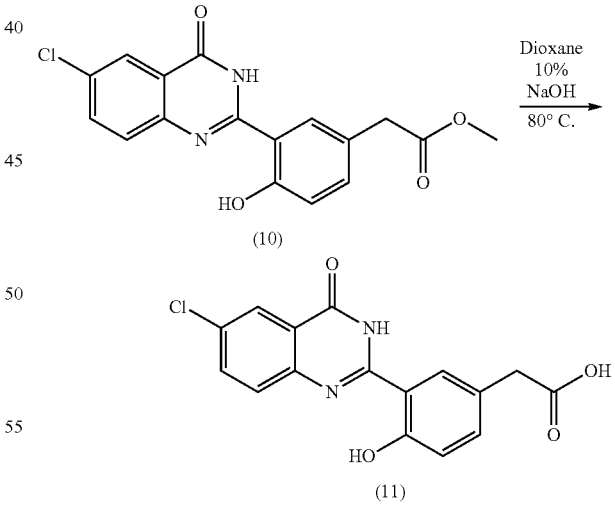

White solid. Yield: 62%. $^1$H NMR (500 MHz, DMSO-d$_6$) δ: 8.17 (d, J=2.4 Hz, 1H), 7.92 (d, J=2.4 Hz, 1H), 7.53 (d, J=2.4 Hz, 1H), 7.52 (d, J=2.4 Hz, 1H), 7.50 (d, J=8.7 Hz, 1H), 7.09 (dd, J=8.3, 2.4 Hz, 1H), 6.59 (d, J=8.3 Hz, 1H), 3.17 (s, 2H). $^{13}$C NMR (126 MHz, DMSO-d$_6$) δ: 189.31, 176.30, 163.44, 161.07, 149.80, 134.18, 132.89, 131.95, 129.28, 128.00, 126.68, 125.25, 123.06, 119.14, 116.99, 45.92.

The ability of fluorophores to precipitate in solution in a similar manner as compound (8) was confirmed. Therefore, fluorophores of Formula (I') could be used as QPDs within the context of the invention.

Example 10: Detection of a Target Bacterial DNA with a Method of the Invention A method of the invention can be used for detection of a target bacterial DNA fragment, for its presence in some material for human or veterinary use such as foodstuff (e.g. that might be present for example in meat or cheese), drinkable preparations, pharmaceutical or cosmetic preparations wherein a test sample is subjected to an isothermal DNA amplification (LAMP), as described in Example 6 and in FIG. 5.

The reaction buffer (e.g. 50-100 microliters) for conducting the amplification reaction comprises:
- 30 mM $NH_4B_5O_8$ (ammonium pentaborate, Sigma)
- 40 mM malic acid (Sigma)
- 8 mM $Mg_2SO_4$ (Sigma)
- 0.8 mM dNTPs (Promega)
- 0.8 M Betaine (5M solution for PCR, Sigma)
- 5% Trehalose (Sigma)
- 0.4 U/microliter Polymerase with strand displacement activity (i.e Bst or GspSSD)
- 0.0004 U/microliter Pyrophosphatase ApePPiase
- 0.1% Triton X-100
- 1.5 microM proprietary primers
- pH 8.5 @25° C.

Target DNA detection is conducted by templated nucleic acid chemistry as described herein.

SEQUENCE LISTING

```
Nucleic acid sequence of probe specific for
porcine DNA
SEQ ID NO: 1:
CTTGGGATGAAC Nucleic acid sequence of probe specific for
porcine DNA
SEQ ID NO: 2:
CTACTAGTTTAGAT Nucleic acid sequence of porcine DNA fragment
SEQ ID NO: 3:
CAGCCCGGAACCCTACTTGGCGATGATCAAATCTATAATG Nucleic acid sequence of probe specific for
porcine DNA
SEQ ID NO: 4:
CGCGACTTGATCCAG Pork DNA region
SEQ ID NO: 5:
GCGCTGAACTAGGTCAGCCCGGAACCCTACTTGGCGATGATCAAATCTAT

AATGTAATTGTTACAGCTCATGCC

Beef DNA region
SEQ ID NO: 6:
GCCTGAATTAGGCCAACCCGGAACTCTGCTCGGAGACGACCAAATCTACA

ACGCAGTTGTAACCGCACACGCA

Horse DNA region
SEQ ID NO: 7:
GTGCTGAATTAGGCCAACCTGGGACCCTACTAGGAGATGATCAGATCTAC

AATGTCATTGTAACCGCCCATGCA

Guinea fowl DNA region
SEQ ID NO: 8:
GCGCAGAACTAGGACAACCAGGGACCCTTTTAGGGGACGACCAAATTTAT

AATGTAATCGTCACAGCCCATGCC

Turkey DNA region
SEQ ID NO: 9:
GGTGCAGAACTGGGACAACCTGGGACACTCCTAGGAGACGACCAAATCTA

TAACGTAATCGTCACAGCCCATGC

Chicken DNA region
SEQ ID NO: 10:
GCGCAGAACTAGGACAGCCCGGAACTCTCTTAGGAGACGATCAAATTTAC

AATGTAATCGTCACAGCCCATGCT

Donkey DNA region
SEQ ID NO: 11:
GTGCTGAATTAGGTCAACCTGGGACCCTGCTGGGAGATGATCAGATCTAC

AATGTTATTGTAACTGCCCATGCA

Monkey DNA region
SEQ ID NO: 12:
GAGCTGAACTAGGCCAACCCGGTAGTTTACTAGGTAGTGACCATATCTAT

AATGTCATTGTGACAGCCCATGCA

Human DNA region
SEQ ID NO: 13:
GAGCCGAGCTGGGCCAGCCAGGCAACCTTCTAGGTAACGACCACATCTAC

AACGTTATCGTCACAGCCCATGCA

Rat DNA region
SEQ ID NO: 14:
GAGCTGAACTAGGACAGCCAGGCGCACTCCTAGGAGATGACCAAATCTAT

AATGTCATCGTCACAGCCCATGCA

Mouse DNA region
SEQ ID NO: 15:
GAGCAGAATTAGGTCAACCAGGTGCACTTTTAGGAGATGACCAAATTTAC

AATGTTATCGTAACTGCCCATGCT

Dromedarius DNA region
SEQ ID NO: 16:
GTGCTGAATTGGGCAGCCTGGGACATTGCTTGGAGATGACCAAATCTAT

AATGTAGTTGTAACGGCTCATGCT

Camel DNA region
SEQ ID NO: 17:
GCGCTGAATTGGGACAGCCCGGGACGTTGCTTGGAGACGACCAAATCTAT

AACGTAGTTGTAACAGCTCATGCT

Lamb DNA region
SEQ ID NO: 18:
GCGCCGAACTAGGCCAACCCGGAACTCTACTCGGAGATGACCAAATCTAC

AACGTAATTGTAACCGCACATGCA

Goat DNA region
SEQ ID NO: 19:
GCGCCGAACTAGGTCAACCCGGAACCCTACTTGGAGATGACCAGATCTAC

AATGTAATTGTAACTGCACACGCA
```

The invention claimed is:

1. A pro-fluorophore of Formula (I):

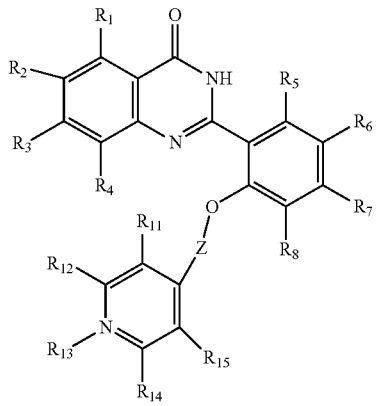

wherein $R_1$ to $R_8$, $R_{11}$-$R_{12}$ and $R_{14}$-$R_{15}$ are independently selected from hydrogen, hydroxyl, halogen, cyano, nitro, optionally substituted $C_1$-$C_{10}$ alkyl, optionally substituted amino $C_1$-$C_{10}$ alkyl, optionally substituted $C_1$-$C_{10}$ alkoxy, $R_{13}$ is selected from optionally substituted $C_1$-$C_{10}$ alkyl, optionally substituted ethyl, optionally substituted propyl or optionally substituted butyl, Z is —$CR_{16}R_{17}$ wherein $R_{16}$ and $R_{17}$ are independently selected from hydrogen and optionally substituted $C_1$-$C_6$ alkyl, or any tautomer, isomer, conjugate or salts thereof.

2. The pro-fluorophore according to claim 1, wherein $R_1$, $R_3$ to $R_5$ and $R_7$ to $R_8$ are H.

3. The pro-fluorophore according to claim 1, wherein $R_2$ is Cl.

4. The pro-fluorophore according to claim 1, wherein $R_2$ is H.

5. The pro-fluorophore according to claim 1, wherein $R_6$ is Cl.

6. The pro-fluorophore according to claim 1, wherein $R_6$ is H.

7. The pro-fluorophore according to claim 1, wherein $R_6$ is substituted amino $C_1$-$C_{10}$ alkyl or alkoxy carbonyl $C_1$-$C_{10}$ alkyl.

8. The pro-fluorophore according to claim 1, wherein $R_{13}$ is selected from substituted propyl, propyl, N-propyl nitrile and optionally substituted butyl.

9. The pro-fluorophore according to claim 1, wherein $R_{16}$ is H.

10. The pro-fluorophore according to claim 1, wherein $R_{17}$ is H.

11. The pro-fluorophore according to claim 1, wherein Z is methyl.

12. The pro-fluorophore according to claim 1, wherein Z is —C(H)(ethyl).

13. The pro-fluorophore according to claim 1, selected from the following group:

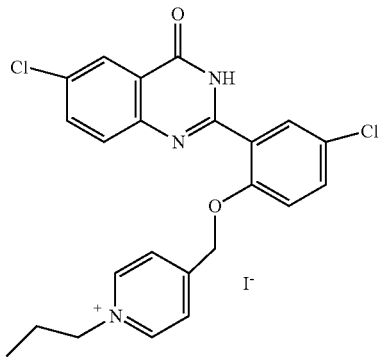

1-propyl-4-((4-chloro-2-(6-chloro-4-oxo-3,4-dihydro quinazolin-2-yl)phenoxy)methyl)pyridin-1-ium;

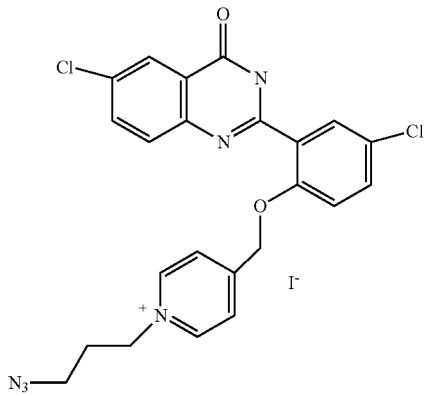

(2)

3-[4-[[4-chloro-2-(6-chloro-4-oxo-3H-quinazolin-2-yl)phenoxy] methyl]pyridin-1-ium-1-yl]propanenitrile;

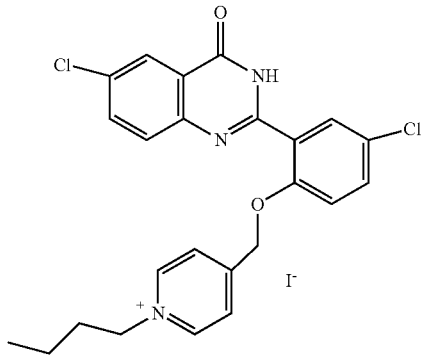

(3)

1-butyl-4-((4-chloro-2-(6-chloro-4-oxo-3,4-dihydro quinazolin-2-yl)phenoxy)methyl)pyridin-1-ium;

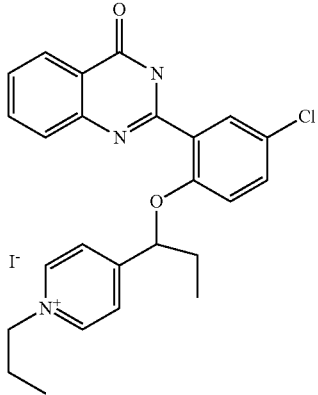 [SMILES: CCC[n+]1ccc(C(CC)Oc2ccc(Cl)cc2-c2nc3ccccc3c(=O)[nH]2)cc1 ; [I-]]

4-(1-(4-chloro-2-(4-oxo-3,4-dihydroquinazolin -2-yl)phenoxy)propyl)-1-propylpyridin-1-ium; 4-((4-chloro-2-(4-oxo-3,4-dihydroquinazolin-2-yl)phenoxy)methyl)-2,6-dimethyl-1-propylpyridin-1-ium

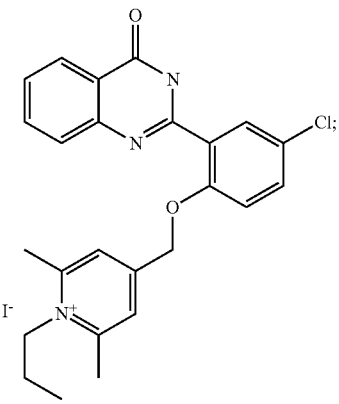 [SMILES: [I-] ; CCC[n+]1c(C)cc(COc2ccc(Cl)cc2-c2nc3ccccc3c(=O)[nH]2)cc1C]

and 4-((2-(4-oxo-3,4-dihydroquinazolin -2-yl)phenoxy)methyl)-1-propylpyridin-1-ium

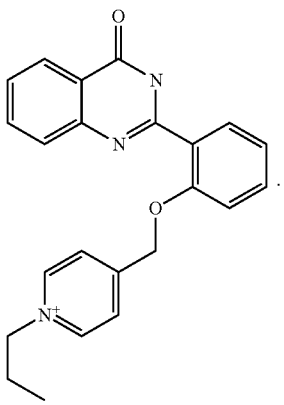

14. A method for the detection of at least one target molecule in a sample comprising a step of contacting a composition comprising a pro-fluorophore according to claim 1 with said sample, the method comprising:
(a) contacting the sample with an anchoring substrate for said at least one target molecule and with a probe for said at least one target molecule, wherein said probe is labelled with a transition metal complex photoredox catalyst, under suitable conditions for the probe to bind the said at least one target molecule and for the target molecule to be anchored onto the surface of said anchoring substrate if the said target molecule is present in the sample;
(b) contacting a composition comprising the pro-fluorophore or a conjugate thereof with the said anchoring substrate, in presence of a reducing agent under suitable condition for inducing a photoredox catalysis of the said pro-fluorophore or a conjugate thereof when the pro-fluorophore is located in the vicinity of the transition metal complex photoredox catalyst; and
(c) detecting the formation of a fluorophore of Formula (I') on said anchoring substrate, wherein the formation of said fluorophore is indicative of the presence of the said at least one target molecule within said sample.

15. The method according to claim 14, wherein said step (a) is achieved through the use of a single type of probe labelled with a transition metal complex photoredox catalyst able to both bind the said at least one target molecule and ensure the anchoring of the target molecule on the substrate or through the use of at least two different types of probes.

16. The method according to claim 14, wherein the conjugate of pro-fluorophore according to Formula (II):

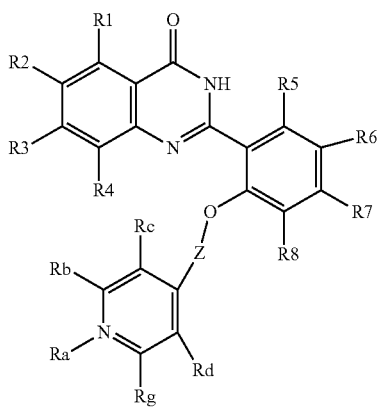

(II)

wherein Ra is a moiety —$R_{13}$-$R_{13a}$, $R_b$ is a moiety —$R_{12}$-$R_{12b}$, $R_c$ is a moiety —$R_{11}$-$R_{11c}$, $R_d$ is a moiety —$R_{15}$-$R_{15d}$, $R_g$ is a moiety —$R_{14}$-$R_{14g}$, wherein $R_1$ to $R_8$, $R_{11}$-$R_{12}$ and $R_{14}$-$R_{15}$ are independently selected from hydrogen, hydroxyl, halogen, cyano, nitro, optionally substituted $C_1$-$C_{10}$ alkyl, optionally substituted amino $C_1$-$C_{10}$ alkyl, optionally substituted $C_1$-$C_{10}$ alkoxy, $R_{13}$ is selected from optionally substituted $C_1$-$C_{10}$ alkyl, optionally substituted ethyl, optionally substituted propyl or optionally substituted butyl, Z is —$CR_{16}R_{17}$ wherein $R_{16}$ and $R_{17}$ are independently selected from hydrogen and optionally substituted $C_1$-$C_6$ alkyl, $R_{11c}$, $R_{12b}$, $R_{13a}$, $R_{14g}$ and $R_{15d}$ are independently optionally present and at least one of the groups $R_{11c}$, $R_{12b}$, $R_{13a}$, $R_{14g}$ and $R_{15d}$ is a linking group of Formula (III):

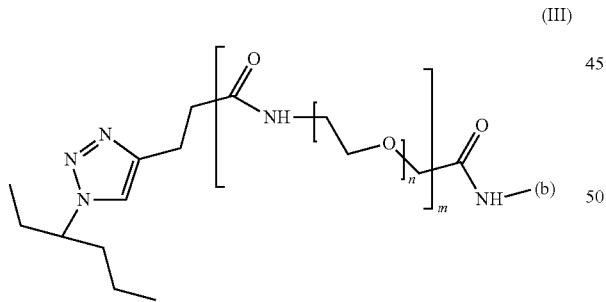

(III)

wherein n is an integer from 1 to 10, m is an integer from 0 to 2 and b is a docking moiety having a specific affinity for the target molecule.

17. A kit for the detection of at least one target molecule in a sample comprising a pro-fluorophore according to claim 1 or a conjugate thereof and optionally, at least one agent selected among a reducing agent and a further probe for the detection of said target molecule.

18. The kit according to claim 17, comprising:
a) at least one probe having a specific affinity for the target molecule labelled with a photoredox catalyst (catalytic probe);
b) at least one probe having a specific affinity for the target molecule labelled with a group for immobilizing the probe to a support (anchoring probe) or labelled with a pro-fluorophore having the structure of Formula (I):

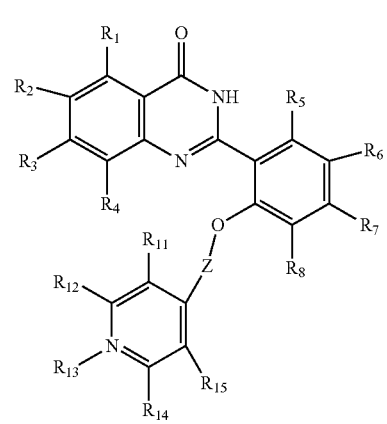

(I)

wherein $R_1$ to $R_8$, $R_{11}$-$R_{12}$ and $R_{14}$-$R_{15}$ are independently selected from hydrogen, hydroxyl, halogen, cyano, nitro, optionally substituted $C_1$-$C_{10}$ alkyl, optionally substituted amino $C_1$-$C_{10}$ alkyl, optionally substituted $C_1$-$C_{10}$ alkoxy, $R_{13}$ is selected from optionally substituted $C_1$-$C_{10}$ alkyl, optionally substituted ethyl, optionally substituted propyl or optionally substituted butyl, Z is —$CR_{16}R_{17}$ wherein $R_{16}$ and $R_{17}$ are independently selected from hydrogen and optionally substituted $C_1$-$C_6$ alkyl, or any tautomer, isomer, conjugate or salts thereof;
c) optionally an anchoring support for immobilizing the target molecule via the anchoring probe;
d) a reducing agent;
e) a pro-fluorophore having the structure of Formula (I):

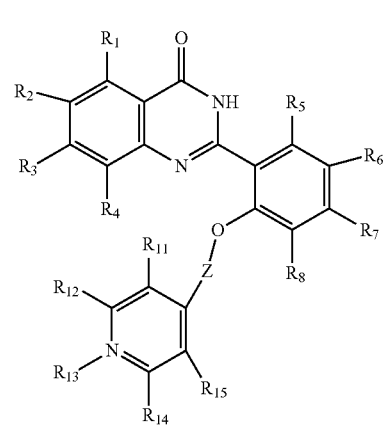

(I)

wherein $R_1$ to $R_8$, $R_{11}$-$R_{12}$ and $R_{14}$-$R_{15}$ are independently selected from hydrogen, hydroxyl, halogen, cyano, nitro, optionally substituted $C_1$-$C_{10}$ alkyl, optionally substituted amino $C_1$-$C_{10}$ alkyl, optionally substituted $C_1$-C10 alkoxy, $R_{13}$ is selected from optionally substituted $C_1$-$C_{10}$ alkyl, optionally substituted ethyl, optionally substituted propyl or optionally substituted butyl, Z is —$CR_{16}R_{17}$ wherein $R_{16}$ and $R_{17}$ are independently selected from hydrogen and optionally substituted $C_1$-$C_6$ alkyl, or any tautomer, isomer, conjugate or salts thereof; and f) optionally at least one vessel for conducting amplification reaction and/or a sampling device.

19. The method according to claim 15, wherein the two different types of probes are:
- a probe that specifically recognizes a portion of a sequence of a target nucleic acid sequence or a complementary sequence to a sequence covalently linked to a sequence string that recognizes the target molecule and ensuring the anchoring of the target molecule on the substrate; and
- a probe that specifically recognizes a portion of a sequence of a target nucleic acid sequence or a complementary sequence to a sequence covalently linked to a sequence string that recognizes the target molecule labelled with a transition metal complex photoredox catalyst.

* * * * *